United States Patent [19]

Iacobucci et al.

[11] Patent Number: 4,638,005

[45] Date of Patent: Jan. 20, 1987

[54] MONOQUATERNIZED PYRAZINIUM COMPOUNDS AND THEIR USE AS ELECTRON CARRIERS IN PHOTOSYNTHETIC PROCESSES

[75] Inventors: Guillermo A. Iacobucci; George A. King; Jacob H. Goldstein, all of Atlanta, Ga.; John R. Benemann, Vallejo, Calif.

[73] Assignee: The Coca-Cola Company

[21] Appl. No.: 476,544

[22] Filed: Mar. 18, 1983

[51] Int. Cl.$^4$ .................. C07D 241/12; C07D 241/18
[52] U.S. Cl. .................................... 544/336; 544/406; 544/408; 585/651
[58] Field of Search .................. 544/336, 406, 408

[56] References Cited

U.S. PATENT DOCUMENTS

| | | | |
|---|---|---|---|
| 2,876,177 | 3/1959 | Gündel et al. | 204/49 |
| 3,183,236 | 5/1965 | Cook et al. | 544/336 |
| 3,679,680 | 7/1972 | Michelson et al. | 544/410 |
| 4,064,124 | 12/1977 | Weitz et al. | 544/336 |
| 4,120,859 | 10/1978 | Pluss et al. | 546/266 |

FOREIGN PATENT DOCUMENTS 1529883  5/1968  France .

OTHER PUBLICATIONS

J. R. Benemann et al., "Advances in Microbial Physiology", vol. 5, Academic Press, 1951, pp. 135-172.
D. I. Arnon, et al., Proc. Nat. Acad. Sci., U.S.A. 78, 2942 (1981).
M. Calvin in "Living Systems as Energy Converters", North Holland Pub. Amsterdam, 1977, pp. 231-259.
E. J. Knight, J. Biol. Chem., 241, 2752 (1966).
T. R. Hamilton, Proc. Natl. Acad, Sci U.S.A., 52, 637 (1966).
J. R. Benemann, Proc. Natl. Acad. Sci U.S.A., 64, 1079 (1969).
J. R. Benemann in "Living Systems as Energy Converters", North Holland Pub., Amsterdam, 1977, pp. 285-297.
B. Kok et al., Biochim, Biophys. Acta, 109, 347-356 (1965).
M. Seibert, E SERI/TP-33-410 U.S. Dept. of Energy Contract No. EG 77CO14042 (1979).
J. Benemann et al., Proc. Natl. Acad. Sci., 70, 2317 (1973).
M. Namiki in C. Eriksson (Ed), "Maillard Reactions in Food", Pergamon Press, Oxford, pp. 81-91.
A. Le Berre, Bull Soc Chim France, 2404 (1973).
L. W. Deady, J. Am. Chem. Soc., 93, 5475 (1971).
A. Le Berre, Bull Soc Chim France, 3, 954 (1970).
E. Hort, J. Am. Chem. Soc., 77, 5898 (1955).
S. Kushner, J. Am. Chem. Soc., 74, 3617 (1952).

*Primary Examiner*—Donald G. Daus
*Assistant Examiner*—William A. Teoli, Jr.
*Attorney, Agent, or Firm*—Kenyon & Kenyon

[57] ABSTRACT

Substituted pyrazinium compounds having at least one polar group such as hydroxyl, carboxyl, carbamido or sulfonoxy can act as high energy electron carriers in photosynthetic processes such as those employing chlorophyll and a reduction enzyme. Such processes with the pyrazinium compounds can produce ammonia and hydrogen.

34 Claims, No Drawings

MONOQUATERNIZED PYRAZINIUM COMPOUNDS AND THEIR USE AS ELECTRON CARRIERS IN PHOTOSYNTHETIC PROCESSES

BACKGROUND OF THE INVENTION

The present invention relates to synthetic pyrazinium compounds and their use in photoreactive enzymatic systems. More specifically, the pyrazinium compounds of the invention are useful as electron carriers in the photoenzymatic production of hydrogen and ammonia.

Photosynthesis is a process that is fundamental for the subsistence of our Biosphere. When carried out by living organisms, this transduction of light energy into chemical energy requires the pigment chlorophyll as a photosensitizer. In higher order organisms, such as eucaryotic organisms, this function is performed in specialized cell organelles, the chloroplasts, which possess many properties like those of an independent organism.

Light energy absorbed by the chloroplasts results in photolysis of water and a potential increase of the photolytically generated "low-energy" electrons (+800 mV) to a "high-energy" value of −600 mV. The "high energy" electrons are trapped by the primary electron carriers found in the chloroplasts. The resulting energy-rich, reduced carriers are then used by the organism to convert carbon dioxide into carbohydrates or hydrocarbons, and nitrogen into ammonia using enzymatically-linked processes. Moreover, under conditions wherein these processes are not fully operative, such as limited access to carbon dioxide or nitrogen, the reduced electron carriers are diverted to a hydrogen production reaction catalyzed with nitrogenase and hydrogenases.

Although the photosynthetic production and utilization processes occurring in chlorophyll organelles are not completely understood, it is known that successive absorption of two light quanta by the coupled chlorophyll pigments P.680 and P.700 is needed in order to raise the energy of electrons produced from water photolysis to that required to produce reduced electron carriers. The high potentials reached by the photoexcited electrons are sufficient to reduce the iron-sulfur clusters present in bound primary electron carriers such as ferredoxin. The energy is then transferred to soluble electron carriers such as free ferredoxin or flavodoxin. Further discussion of the biological photosynthetic process may be found in J. R. Benemann, et. al., "Advances in Microbial Physiology", Vol. 5, Academic Press London, 1971, pp. 135–172; D. I. Arnon, et al., *Proc. Nat. Acad. Sci. USA,* 78, 2942-6 (1981); M. Calvin, in "Living Systems As Energy Converters", North Holland Pub., Amsterdam, 1977, pp. 231–259.

Proteins such as ferredoxins and flavodoxins are the natural electron carriers present in biological organisms that participate in the in vivo transfers of high energy electrons in both aerobic and anaerobic processes, see E. J. Knight, et al., *J. Biol. Chem.,* 241, 2752 (1966). These proteins participate in in vivo light dependent nitrogen fixation, carbohydrate production and hydrogen evolution as well as light independent anaerobic nitrogen fixation, see T. R. Hamilton, et al., *Proc. Natl. Acad. Sci. USA,* 52, 637 (1964). Essentially, they carry the high energy electrons from chlorophyll to the enzymes which use them.

Artificial systems using ferredoxins and flavodoxins have been developed recently as part of several investigations of the synthetic production of hydrogen by photolysis of water. Such systems have also been utilized as test assay models for the study of photosynthetic reactions. Typically, the system can employ a synthetic photo-activator or isolated plant chloroplasts, an electron carrier and an enzyme such as nitrogenase or hydrogenase, see J. R. Benemann, et al., *Proc. Nat. Acad. Sci. USA,* 64, 1079 (1969); and J. R. Benemann in "Living Systems As Energy Converters", North-Holland Publ., Amsterdam, 1977, pp. 285–297. In such a model, for example, the activity of the system stimulated by the photosynthetic reaction is followed by the reduction of acetylene to ethylene.

Studies using isolated chloroplast systems have shown that other compounds can function as electron carriers and can be substituted for ferredoxin or flavodoxin. For example, dipyridyls such as methyl viologen, benzyl viologen and cyclic analogs thereof are able to couple illuminated chloroplasts and the enzyme hydrogenase, see K. K. Rao, et al., in "Photosynthesis In Relation to Model Systems," pp. 299–329, Elsevier, Amsterdam, 1979; I. Okura, et al., *J.C.S. Chem. Comm.,* 1980, 84. These synthetic compounds can also interact in cellular photochemical redox reactions to cause "short circuiting" of the photosynthetic pathways. It is not surprising, therefore, to find that a few dipyridyls such as diquat and paraquat have herbicidal activity, see B. Kock, et al., *Biochem Biophys. Acta,* 1091, 347 (1965).

Generally, however, very few organic compounds are known to function effectively as electron carriers for chloroplast or synthetic photo-activator systems. Typically, the potentials of the reduced forms of known low molecular weight organic carriers do not match the potential required for effective enzyme coupling. As a consequence, transfer of the energetic electrons by these carriers becomes inefficient. Moreover, any tendency of the reduced forms of the carriers to remain bound to the chloroplast favors the undesirable reverse reaction with the organelle which will cause failure of the electron transfer process. Synthetic electron carriers designed and synthesized from protein material, such as synthetic analogs of flavodoxin or ferredoxin, are also theoretically possible. Their syntheses, however, would be complicated, their half lives short and they would require special process and synthetic measures incident to the use of proteins. Accordingly, the nature of the carrier is one of the limiting features of an artificial photosynthetic system.

It is, therefore, an object of the invention to develop synthetic organic compounds which can function as efficient electron carriers in a chloroplast or synthetic photo-activator photosynthetic system. Another object is the production of a stable organic compound which will increase the efficiency of a photosynthetic system. A further object is the production of an organic compound which is highly stable in a reduced, energetic state. Yet another object is the production of water-soluble organic compounds which maximize the transduction process utilizing the chloroplast organelle.

SUMMARY OF THE INVENTION

These and other objects are achieved by the present invention which is directed to monoquaternized pyrazinium compounds which facilitate the photosynthetic production of hydrogen, ammonia and carbohydrates. In particular, the invention is directed to monoquaternized pyrazinium compounds of formula I which can transfer high energy electrons from an electron photo-activating source.

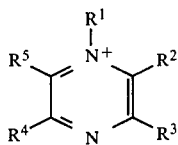

In formula I, $R^1$ is alkyl of 1 to 3 carbons, (sulfonoxy)alkyl of 1 to 3 carbons or (carboxy)alkyl of 3 to 4 carbons.

$R^2$, $R^4$, and $R^5$ are independently selected from hydrogen or alkyl of 1 to 3 carbons.

$R^3$ is sulfonoxy or a group of the formula $(CH_2)_n CHXY$; wherein X is hydrogen, hydroxy, sulfonoxy, carboxy, carboxamido, (sulfonoxy)alkyl of 1 to 3 carbons, dihydroxyalkyl of 2 to 3 carbons or (carboxy)alkyl of 2 to 3 carbons; Y is hydrogen, (sulfonoxy)alkyl of 1 to 3 carbons, alkyl of 1 to 3 carbons or dihydroxyalkyl of 2 to 3 carbons; and n is a whole number from 0 to 6, when either of X or Y constitutes a sulfonoxy group, a (sulfonoxy)alkyl group or together they constitute multiple polar groups; otherwise n is 0 to 3.

X and Y, together, constitute multiple polar groups when X is selected from hydroxy, sulfonoxy, carboxy, carboxamido, (sulfonoxy)alkyl, dihydroxyalkyl or (carboxy)alkyl and when Y is selected from (sulfonoxy)alkyl or dihydroxyalkyl.

For formula I, it is provided that when $R^1$ is alkyl, $R^3$ is other than alkyl; and when $R^1$ and $R^3$ together contain other than a carboxy or sulfonoxy substituent, a gegenion is also present.

In the context of this invention, a gegenion is an anion which functions as the counter ion of the monoquaternary pyrazinium salt compound of formula I when an anionic group at substituents $R^1$ and $R^3$ is absent from formula I. When such an anionic group is present, a gegenion is not necessary since the resulting compound is zwitterionic. Anions which function in this capacity are those of corresponding mineral or organic acids. Examples include but are not limited to halide, sulfate, bisulfate, phosphate, biphosphate, nitrate, perchlorate, borate, citrate, tartrate, acetate, propionate, succinate, benzoate and the like.

Also, in the context of this invention, the term "sulfonoxy" is defined as the radical derived from sulfonic acid, $-SO_3H$. Thus, (sulfonoxy)ethyl is $-CH_2CH_2SO_3-$ and (sulfonoxy)ethyl benzene would be formulated as $C_6H_5CH_2CH_2SO_3-$.

The invention is further directed to the isolated, purified forms of the compounds of formula I as well as the synthetically produced compounds of formula I.

Preferred embodIments of the compounds of formula I include those having the following moieties for substituents $R^1$ through $R^5$, X and Y:

(a) compounds of formula I wherein $R^1$ is alkyl;

(b) compounds of formula I wherein $R^3$ is a group of the formula $(CH_2)_n CHXY$;

(c) compounds of formula I wherein $R^2$ is hydrogen;

(d) compounds of formula I wherein $R^2$, $R^4$ and $R^5$ are independently selected from hydrogen or methyl;

(e) compounds of formula I wherein $R^1$ is (sulfonoxy)alkyl;

(f) compounds of formula I wherein $R^3$ is sulfonoxy or a group of the formula $(CH_2)_n CHXY$ and X is hydroxy, carboxy, carboxamido, sulfonoxy, (sulfonoxy)alkyl, (carboxy)alkyl or dihydroxyalkyl;

(g) compounds as described in (f) wherein $R^2$ is hydrogen;

(h) compounds of formula I wherein $R^3$ is sulfonoxy or a group of the formula $(CH_2)_n CHXY$, and X is sulfonoxy, hydroxy or (sulfonoxy)alkyl; and (i) compounds as described in (h) wherein $R^3$ is a group of the formula $(CH_2)_n CHXY$.

Especially preferred compounds of formula I are those having the following groups for substituents $R^1$ through $R^5$, X and Y; the names of these compounds are also specified.

1. $R^2$, $R^4$ and $R^5$ are all hydrogen, $R^1$ is methyl, and $R^3$ is 1-hydroxyethyl; 1-methyl-3-(1-hydroxyethyl)-pyrazinium iodide.

2. $R^2$, $R^4$ and $R^5$ are all hydrogen, $R^1$ is methyl, and $R^3$ is 2-hydroxyethyl; 1-methyl-3-(2-hydroxyethyl)-pyrazinium iodide.

3. $R^2$ and $R^5$ are both hydrogen, $R^1$ and $R^4$ are methyl, and $R^3$ is hydroxymethyl; 1,5-dimethyl-3-hydroxymethylpyrazinium iodide.

4. $R^2$ and $R^4$ are all hydrogen, $R^1$ and $R^5$ are methyl, and $R^3$ is hydroxymethyl; 1,6-dimethyl-3-hydroxymethylpyrazinium iodide.

5. $R^2$, $R^4$ and $R^5$ are all hydrogen, $R^3$ is methyl, $R^1$ is 3-sulfonoxypropyl; 1-(3-sulfonoxypropyl)-3-methylpyrazine.

6. $R^3$ and $R^5$ are hydrogen, $R^2$ and $R^4$ are both methyl, and $R^1$ is 3-sulfonoxypropyl; 1-(3-sulfonoxypropyl)-2,5-dimethylpyrazine.

7. $R^2$, $R^4$ and $R^5$ are all hydrogen, $R^1$ is methyl, n is 1, Y is ethyl and X is sulfonoxy; 1-methyl-3-(2-sulfonoxybutyl)pyrazine.

8. $R^2$, $R^4$ and $R^5$ are all hydrogen, $R^1$ is methyl, n is 2, Y is n-propyl and X is sulfonoxy; 1-methyl-3-(1-sulfonoxybutyl)pyrazine.

9. $R^2$, $R^4$ and $R^5$ are all hydrogen, $R^1$ is methyl, n is 2 and X is 1,2-dihydroxyethyl; 1-methyl-3-(3,4-dihydroxybutyl)pyrazinium iodide.

10. $R^2$, $R^4$ and $R^5$ are all hydrogen, $R^1$ is methyl, n is 0 and X and Y are 2,3-dihydroxypropyl; 1-methyl-3-(1,2,6,7-tetrahydroxyhept-4-yl)pyrazinium iodide.

11. $R^2$, $R^4$ and $R^5$ are all hydrogen, $R^1$ is methyl, n is 0 and X and Y are both 3-sulfonoxypropyl; sodium 4-(1-methyl-3-pyrazinyl)heptane-1,7-disulfonate.

12. Y, $R^2$, $R^4$ and $R^5$ are all hydrogen, $R^1$ is methyl, n is 3 and X is sulfonoxy; 1-methyl-3-(4-sulfonoxybutyl)-pyrazine.

13. Y, $R^2$, $R^4$ and $R^5$ are all hydrogen, $R^1$ is methyl, n is 0 and X is sulfonoxy; 1-methyl-3-sulfonoxypyrazine.

14. $R^2$, $R^4$, $R^5$ and Y are all hydrogen, $R^1$ is methyl, n is 0, and X is 1,2-dihydroxyethyl; 1-methyl-3-(1,2-dihydroxyethyl)pyraziniuim iodide.

15. $R^2$, $R^4$, and $R^5$ are all hydrogen, $R^1$ and Y are methyl, n is 0 and X is sulfonoxy; 1-methyl-3-(1-sulfonaxyethyl) pyrazine.

16. $R^2$, $R^4$, $R^5$ and Y are all hydrogen, $R^1$ is methyl, n is 1 and X is sulfonoxy; 1-methyl-3-(2-sulfonoxyethyl)-pyrazine.

17. $R^2$, $R^4$, Y and $R^5$ are all hydrogen, $R^1$ is both methyl, n is 0 and $R^3$ is sulfonoxy; 1-methyl-3-sulfonoxymethylpyrazine.

18. Y, $R^2$ and $R^5$ are hydrogen, $R^1$ and $R^4$ are methyl, n is 0 and X is sulfonoxy; 1,5-dimethyl-3-sulfonoxymethylpyrazine.

19. Y, $R^2$ and $R^4$ are hydrogen, $R^1$ and $R^5$ are methyl, n is 0 and X is sulfonoxy; 1,6-dimethyl-3-sulfonoxymethylpyrazine.
20. $R^2$, $R^4$ and $R^5$ are hydrogen, $R^1$ is methyl, n is 1, X is hydroxy and Y is ethyl; 1-methyl-3-(2-hydroxybutyl) pyrazinium iodide.
21. $R^2$, $R^4$ and $R^5$ are hydrogen, $R^1$ is methyl, n is 1, X is sulfonoxy and Y is 1,2-dihydroxyethyl; 1-methyl-3-(2-sulfonoxy-3,4-dihydroxybutyl) pyrazinium salt.

In addition, the isolated, purified forms of the synthetically produced compounds 1 through 21 are especially preferred.

The invention further is directed to a method for transferring high electrons from an electron photoactivating source. The method comprises combining the source with pyrazinium compounds of formula I wherein $R^3$ is hydrogen, sulfonoxy or a group of the formula $(CH_2)_n CHXY$.

When combinations of biological materials including such a source are made, the system can biophotosynthetically manufacture carbohydrates, hydrogen or ammonia. It can constitute a combination of natural, in vivo biological organisms or can constitute in vitro combinations of synthetic compounds and biological material which may be isolated from biological organisms or synthetically or genetically produced. In addition, the systems may also be constructed entirely of synthetic material designed to produce such products photosynthetically.

In particular, the system comprises a photo-activating source agent such as chloroplasts, in combination with water, a compound of formula I, and a coupled reductive enzyme such as hydrogenase or nitrogenase.

In a preferred embodiment, chloroplasts are employed in a two stage system having the chloroplasts, compound and water in one stage and the enzyme, compound and water in the other. The stages are connected with a semipermeable membrane which allows passage of the compound but not of the chloroplasts or enzyme. Appropriate ancillary ingredients such as adenosine triphosphate, salts and gases are also present in the aqueous medium. Product gases from each stage are collected separately so that short circuiting will not occur.

Use of in vivo organisms would include for example enhancement of nitrogen fixation by rhizobia by contacting rhizobia with a pyrazinium compound. Other photo-activating sources which may be used with the pyrazinium compounds include synthetic agents such as ruthenium, molybdenum or iron-organometallic complexes with such groups as bipyridyl or porphyrin.

These and other features of the invention are explained in greater detail in the following description of the invention.

DETAILED DESCRIPTION OF THE INVENTION

The monoquaternized pyrazinium compounds of the invention are effective electron carriers for "high energy" electrons produced in particular by chlorophyll photosynthesis. In this process, they are repeatedly able to transfer "high energy" electrons from illuminated chloroplasts to a photosynthetically coupled enzyme such as nitrogenase. They also may be able to function as effective carriers for "high energy" electrons produced by synthetic photosensitizer organometallic complexes such as ruthenium, molybdenum and iron complexes.

In general, they are water soluble and have a reduction potential lower than about −500 millivolts as measured by a polarographic half wave potential at pH 7.5. The reduction potential, however, is a threshhold requirement; below this minimum, activity is determined by chemical structure.

When incorporated into a photosynthetic system, the pyrazinium compounds of the invention function as coupling agents tying together the photolytic reaction producing high energy electrons and the reductive reaction using the high energy electrons to synthesize products, typically hydrogen or ammonia. They transfer the energy from one reaction to the other and in the process, maintain their structural and chemical integrity. In the reduced state, they are substantially stable and do not undergo degradative side reactions to a substantial extent. This property permits coupling of the photolytic and reductive reactions with no appreciable loss in energy and allows the efficient transduction of energy. Furthermore, in their capacity as coupling agents, the compounds of the invention undergo multiple redox reactions. Nevertheless, the repeated oxidation and reduction do not substantially modify the chemical nature of the compounds. They are capable of functioning in a multitude of redox events without breakdown or degradation. Consequently, an operating photosynthetic system does not require large amounts of compound in order to carry out electron transfers.

The ability of the compounds of the invention to function as electron carriers is accomplished by a combination of chemical structure features. The pyrazine nucleus should be monoquaternized and a polar substituent should be present which can exist in a form that can provide labile hydrogens and can hydrogen bond. In general, this substituent will contain hydroxyl, carboxyl, carboxamido or sulfonoxy groups and the like which will provide the polar, proton-donating, hydrogen-bonding character. Substituent groups such as ether groups, ketone groups, substituted amide groups and alkyl sulfone groups, however, have been found in particular instances not to generate carrier activity. A preferred substituent is an alkyl side chain substituted with one or more polar groups such as hydroxyl, carboxyl, carboxamide and/or sulfonoxy. The side chain may be the monoquaternizing group or it may be in a 1,3 substitution with respect to the quaternized nitrogen. Generally, the length of the alkyl side chain will depend upon the number and kind of polar groups present. When the polar group is sulfonoxy or multiple combinations of hydroxyl, carboxyl, carboxamide or sulfonoxy groups, the chain size may be up to about ten carbons. Otherwise, the chain size may be up to about seven carbons.

These specifications are met by the compounds of foregoing formula I. Other, similar chemical formulas for monoquaternized pyrazinium compounds based upon formula I and the foregoing specifications will be apparent to those skilled in the art. These compounds are also included in the present invention provided that they have a first reduction potential between about −500 and −800 millivolts at pH7.5, as measured by a polarographic half wave potential.

The synthesis of the pyrazinium compounds of formula I is generally based upon known chemical conversions for substituted pyrazines and organic functional groups. Combination of these conversions produces the methods for preparation of the pyrazinium compounds of the invention. The methods generally will employ nucleophilic substitution of, and addition to 2-chloro or bromopyrazines as well as base catalyzed condensation of 2-alkyl pyrazines with ketones, aldehydes, esters, sultones, sulfonic esters and the like. Multifunctional side chains can be synthesized from substituted pyrazine intermediates having a synthon group appropriately positioned within the substituent. These methods will be apparent from the following description and schemes.

The methods can be divided into two phases: synthesis of pyrazine compounds having polar substituents and monoquaternization of the pyrazine nucleus to form the pyrazinium compounds. Of course, if the monoquaternizing group is also the polar substituent, these phases are combined. Accordingly, the term "pyrazine compounds" will hereinafter be taken to mean the unquaternized form of the pyrazinium compounds of the invention.

The general methods for pyrazine compound synthesis as well as specific methods for functionally substituted pyrazine compound synthesis and the methods for quaternization are illustrated by Schemes A through N. Schemes A through D show the synthesis of the substituted pyrazine intermediate synthons upon which the general synthesis is based as well as the general synthesis of monofunctionally substituted pyrazine compounds. Schemes E through J show the general synthesis of pyrazine compounds with multifunctional side chains from the intermediate synthons. Schemes K through M show specific methods for the synthesis of pyrazine compounds. Scheme N shows methods for monoquaternization of the pyrazine compounds to form the pyrazinium compounds of the invention. In these schemes and the discussion hereinafter, the pyrazine nucleus with an alkyl side chain, having the formula

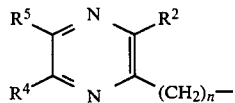

shall be designated as "Het".

Scheme A teaches a method for synthesis of intermediate Aldehyde 4 which is a useful synthon for the preparation of penultimate pyrazine compounds of the invention. The carbonyl carbon of Aldehyde 4 is a bifunctional site which can be used to attach multiple functional groups to the Het nucleus. Scheme A also teaches methods for synthesis of monofunctionalized pyrazine compounds such as Sulfonic Salt 5, Carboxylic Acid 6 and Ester 7. Compounds 5, 6 and 7 may be synthesized as well by the methods of Schemes K through M.

In general, it will be noted that many of the pyrazine compounds are substituted with sulfonate radicals or carboxylate radicals. These compounds can be prepared as the salts, such as the alkali metal or alkaline earth metal sulfonates and carboxylates or as the acids, such as the sulfonic acid. Moreover, they can also be prepared as the simple alkyl esters. The salt, acid and ester forms are interconvertable by methods known to those skilled in the art, for example, esterification with diazoalkane, neutralization of the acid with alkali, direct preparation of the salt or conversion of the salt to the acid. All three forms are contemplated by the invention. For convenience, the salt form, hereinafter designated by E, is discussed.

According to Scheme A, Aldehyde 4 is prepared from Halo (chloro or bromo) pyrazine 1 which is substituted with groups $R^2$, $R^4$ and $R^5$ as defined according to formula I. Halopyrazine 1 is first condensed with the protected hydroxyalkyl Grignard Reagent I as shown in reaction A1. The protecting group $R^6$ of Reagent I is an alcohol protecting group such as tetrahydropyranyl (THP) group or a trialkylsilyl group $R_3Si$, e.g. trimethyl silyl or t-butyl dimethyl silyl, or similar known hydroxy protecting groups stable to carbanions. The reaction is conducted in an aprotic, dry organic solvent such as an ethereal or hydrocarbon solvent at cold to mild temperatures to produce Protected Hydroxy Het Compound 2. As shown by Scheme A reaction A2, treatment of Compound 2 with the appropriate reagent to remove the protecting group will produce Alcohol 3, e.g., THP removal by a cold, mild aqueous acid such as dilute aqueous acetic acid or $R_3Si$ removal by tetra-n-butyl ammonium fluoride in a polar organic solvent under mild to vigorous conditions or by moderate alcoholic mineral acid. In addition to being an intermediate, Alcohol 3 is a pyrazine compound (X is hydroxy, Y is hydrogen).

As shown in reaction A3, Alcohol 3 can be converted to Aldehyde Synthon 4 by gentle oxidation, such as a cold Jones acidic chromium trioxide oxidation in acetone or similar solvent under cool conditions or a Corey chromium trioxide pyridinium complex oxidation in methylene chloride or a similar solvent at ice bath or cold temperatures. It may also be converted to Acid Pyrazine Compound 5, as shown in reaction A4 by a vigorous acidic chromium troxide or permanganate oxidation. Additionally, any of the other known methods for preparation of aldehydes and acids from alcohols may be used, see, for example, "Reagents For Organic Synthesis" by L. F. and M. Fieser, Wiley Interscience, N. Y.

Acid 5, in turn, may be esterified as shown in reaction A6 to produce Alkyl Ester Pyrazine Compound 7 by known methods such as treatment with diazoalkane or treatment with alkanol and hydrogen chloride.

Sulfonic Salt Pyrazine Compound 6 is produced from Alcohol 3, as shown in reaction A5, by nucleophilic substitution of the functionalized hydroxy group with sulfite ion. To facilitate the substitution, the Alcohol 3 may be converted to a bromide and treated with sodium sulfite in polar aprotic solvent. The preferred method for preparation of Sulfonic Salt 6 is conversion of Alcohol 3 to a tosylate by its reaction with p-toluene sulfonyl chloride (tosyl chloride or TsCl) in a dry solvent such as ethereal solvent, chloroform, methylene chloride, dimethyl formamide and the like, and in the presence of a scavenging amount of pyridine, followed by substitution of the tosylate with sulfite. Typical reaction conditions will be use of a polar such as water or alcohol solvent and mild to moderate temperatures. Although the sulfonic acid can be obtained by treatment of the resulting salt with a mineral acid, the sulfonic compound is typically isolated in salt form such as the sodium sulfonate. The salt is directly produced by the sulfite substitution of the tosylate. Methods for these conversions are also well-known in the art.

Schemes B, C and D represent a series of chemical group transformation steps which are repeatedly used in the pyrazine compound syntheses shown by Schemes E through J. For brevity, these steps are discussed separately as Schemes B, C and D. As will be apparent from the ensuing discussion, the steps of Schemes B, C and D, and also, several of the steps of Scheme A, are used to prepare pyrazine compounds from Aldehyde 4, i.e., formula II, HetCOR", wherein R" is hydrogen, or from its functionalized ketone derivative of formula II, Het-COR" wherein R" is a group prepared and defined by the preceding synthetic steps. "HetCOR" is hereinafter termed Aldehyde/ketone II.

Scheme B depicts a sequence of steps which can be used to prepare intermediates leading to the preparation of pyrazine compounds substituted with a sulfonic acid group. As shown in reaction B1 of this sequence, Aldehyde/ketone II can be reacted in dry ethereal solvent and under mild to cool temperature conditions, with protected hydroxy alkyl Grignard reagent of formula III, $ZMg(CH_2)_kOR^7$, wherein Z is chloro or bromo, k is a number selected from 2 to 3 and $R^7$ is a known hydroxyl protecting group stable to Grignard, such as THP or $SiR_3$, to produce Alcohol 8. When R' of Alcohol 8 is hydrogen, it can be oxidzed, as shown in reaction B2, to Ketone 9 by known methods such as by treatment with oxidizing agents such as chromium trioxide, permanganate and the like. Alternatively, Alcohol 8 can be converted, as shown in reaction B3, to the corresponding Tosylate 10 by treating it with TsCl as described above (reaction A5).

In a second part of the sequence of Scheme B, pyrazine compounds having a sulfonic acid group one methylene away from the bifunctional site are prepared using methylsulfonic acid methyl ester. As shown in reaction B4, Aldehyde/ketone II can be condensed, with the carbanion of methylsulfonic acid methyl ester in dry aprotic organic solvent such as ethereal solvent, or an excess of the ester itself followed by trapping the in situ produced alkoxide with trialkyl silyl chloride, to produce Silyl Sulfonate Compound 11. When R' is hydrogen for Compound 11, as shown in reaction B5, the silyl group can be cleaved with aqueous tetra-n-butyl ammonium fluoride followed by oxidation of the resulting secondary alcohol by any of the known alcohol to ketone oxidation methods, see L. F. Fieser, cited above, to produce Ketosulfonate 12.

As shown by the third part of Scheme B, reaction B6, a similar sequence employs a Wittig reaction. Aldehyde/ketone II can also be reacted in a Wittig reaction with Sulfonate ylid IV in ethereal solvent and under moderate conditions to produce Olefinic Sulfonate 13. Procedures for the Wittig reaction are also known.

As shown by the fourth part of Scheme B, reaction B7, Tosylate 10 can be reduced with an alkali metal borohydride such as sodium borohydride in polar solvent and under mild to moderate conditions replace the tosylate group with a hydride. Pyrazine compound 10-B is produced in this manner. This tosylate reduction as well as other useful hydroxy conversions are discussed in "Compendium of Organic Synthetic Method", I. Harrison, S. Harrison, Wiley-Interscience, N.Y. 1981.

Scheme C depicts a sequence of steps which can be used for preparation of an olefinic intermediate leading to pyrazine compounds substituted with a dihydroxyalkyl group. As shown by reaction C1, Aldehyde/ketone II is reacted with vinyl lithium or alkyl Grignard reagent V to produce Olefinic Alcohol 14. Typically, this known transformation will be conducted in dry ethereal solvent under mild to moderate temperature conditions. Olefinic Alcohol 14 may then be transformed into Olefinic Ketone 15, Olefinic Tosylate 16 or Acetal Ketone 17 as follows. When R' of Alcohol 14 is hydrogen, as shown by reaction C2, oxidation of Alcohol 14 by the methods described above will produce Ketone 15. As shown by reaction C3, treatment of Alcohol 14 with tosyl chloride under the conditions described above will yield Tosylate 16.

As shown by reaction C4, mild oxidation of the olefinic group of Ketone 15 with cold osmium tetroxide or cold potassium permanganate in a polar solvent will convert the olefin group to a diol group. Any of the other known methods for diol preparation from olefins may also be used, see for example "Advanced Organic Chemistry" 2nd Ed., J. March, McGraw-Hill, 1976. Treatment of the diol with a ketone such as acetone or methyl ethyl ketone in acidified organic polar solvent yields Acetal Ketone 17.

Scheme D depicts a sequence of steps which can be used for preparation of a protected alkyl carboxylic acid intermediate leading to pyrazine compounds substituted with a (carboxy)alkyl group. As shown by reaction D1, Aldehyde/kentone II is reacted with protected carboxy Grignard Agent VI in ethereal solvent under mild conditions, as mentioned above, to yield, upon hydrolysis, Protected Carboxy Compound 18. Any carboxy protecting group which is stable to Grignard conditions can be used for Agent VI. The oxazidine group shown in Scheme D is an example. It is stable to Grignard reagents and oxidation, but can be removed with ethanolic HCl, see for example, "Compendium of Organic Synthetic Methods", I. Harrison, S. Harrison, Wiley-Interscience, N.Y. 1971.

As shown by reaction D2, the hydroxy group of Compound 18 may be converted to a hydride group by borohydride reduction of the tosylate formed from the hydroxy group. Compound 18 is first treated with alcohol and acid to remove the carboxyl protecting group and form an ester. The hydroxyl group of the resulting omega-hydroxy ester is tosylated under conditions as described above, then the tosylate group is reduced with sodium borohydride or a similar borohydride in polar solvent under mild to moderate conditions to yield Ester 19. When R' of Compound 18 is hydrogen, as shown by reaction D3 the hydroxy group of Compound 18 may be oxidized to a ketone group by any of the known hydroxyl oxidation methods mentioned above, and produce Ketone 20.

Multifunctional pyrazine compounds according to the invention can be prepared as depicted in Schemes E through J. The synthetic steps outlined by these schemes are generally known. The schemes vary as a function of the definition of substituent X.

Scheme E depicts the synthesis of multifunctional pyrazine compounds having X as hydroxy. In this scheme, as shown by reactions E1 and E2, Hydroxy Sulfonic Acid Pyrazine Compound 22 is produced from intermediate Silyl Sulfonic Salt 21 and Sulfonate Compound 11. Salt 21, in turn, is produced from Alcohol 8 of reaction B1. The free hydroxy group of Alcohol 8 is first protected as a trialkyl silyloxy group using trialkyl silyl chloride as described above, then the THP group is selectively cleaved with cold, mild aqueous acid to produce a silyloxy alcohol (not shown). This alcohol compound can then be converted to Silyl Sulfonic Salt 21 by the bromide or tosylate method described above for Scheme A (reaction A5). Removal of the silylhydroxy protecting group of Sulfonic Salt 21 and of Compound 11 by the methods described above for scheme A (reaction A2), followed by hydrolysis of the ester group of 11, produces Hydroxy Sulfonic Salt Pyrazine Compound 22.

As shown by reaction E3, Olefinic Alcohol 14 can be converted into Trihydroxy Pyrazine Compound 23 by olefinic oxidation. Alcohol 14 is treated with an olefinic oxidizing agent as described for Scheme C (reaction C4) to produce Compound 23.

Finally, as shown by reaction E4, Aldehyde 4 from Scheme A can be reacted with an alkyl Grignard reagent of 1 to 3 carbons, under the usual conditions for Grignard reactions, to produce Secondary Hydroxy Pyrazine Compound 24.

Scheme F depicts the synthesis of multifunctional pyrazine compounds having X as carboxyl. As shown by reaction F1, F2 and F3, Carboxylate 26 is produced from a Cyanide Intermediate, 25a and 25b. Tosylate 10 from reaction B3 is reacted with cyanide in polar organic solvent and mild to vigorous conditions to produce Cyanide 25a. In a similar fashion, Olefinic Sulfonate 13 from reaction B6 can be reacted with cyanide in polar organic solvent to produce Cyanide 25b. Cyanide 25a, in turn, can be converted to the corresponding Carboxyl Sulfonoxy Pyrazine Compound 26, as shown by reaction F3, by the tosylate-sulfonate transformation, conducted according to the description for reactions A2 and A5, and subsequent nitrile hydrolysis in aqueous, strong acid with optional alcohol and heating. Cyanide 25b is similarly converted to the corresponding Carboxyl Sulfonoxy Pyrazine Compound 26 by hydrolysis of the nitrile group.

Reactions F5 and F6 show the preparation of Dihydroxy Carboxy Pyrazine Compound 28. Olefinic Ketone 15 from reaction C2 is treated with dibromoylid reagent VII followed by reaction of the resulting dibromoolefin with an alkoxide such as sodium methoxide in methanol to produce the corresponding alkyl vinyl ether compound (not shown). This compound is treated with acidic alcohol to produce Olefinic Carboxylic Acid 27. Acid 27 is then oxidized with an olefinic oxidation reagent, under conditions as described for reaction C4, to produce Pyrazine Compound 28.

Reaction F7 shows the preparation of Alkyl Carboxy Pyrazine Compound 29. Treatment of Aldehyde 4 with an alkyl Grignard reagent of 1 to 3 carbons, conversion of the resulting alkyl alcohol to a tosylate, under the conditions described for reaction A5, nucleophilic substitution of the tosyl group by cyanide and subsequent hydrolysis, under the conditions described for reaction F3, will produce Pyrazine Compound 29.

Scheme G depicts the synthesis of multifunctional pyrazine compounds having X as a sulfonoxy group. Reactions G1 and G2 show the preparation of Disulfonic Acid Pyrazine Compound 31 from Alcohol 8 and Sulfonate 13. These reactions follow the methods described for reaction A5 and a dibromo compound or a ditosylate compound may be used as the intermediate. Alcohol 8 from reaction B1 is first hydrolyzed (reaction G1, conditions as described for reaction A2) to remove the alcohol protecting group. The resulting dihydroxy compound (not shown) is ditosylated to produce Ditosylate 30. Ditosylate 30 or the other intermediate, Olefinc Sulfonate 13 from reaction B6, may then be reacted with sulfite anion as shown by reaction G2 to produce Pyrazine Compound 31.

Reactions G3 and G4 show the preparation of Dihydroxy Sulfonate Pyrazine Compound 33. Tosylate 16 (R' is hydrogen) from reaction C3 is first reacted with sulfite anion, as described for reaction A5, to produce Olefinic Sulfonic Acid 32 which is oxidized with an olefinic oxidizing agent, as described for reaction C4, to produce Pyrazine Compound 33.

Finally, as shown by reaction G5, Alkyl sulfonic Acid Pyrazine Compound 34 is prepared by reaction of Aldehyde 4 with an alkyl ($R^9$) Grignard reagent, followed by the reaction A5 tosylate-sulfonate transformation of the resulting alcohol.

Scheme H depicts the synthesis of multifunctional pyrazine compounds having X as a (sulfonoxy)alkyl group of 1 to 3 carbons. Reactions H1 through H3 show the preparation of Bis(sulfonoxy)alkyl Pyrazine Compounds 36 and 37. Ester 7 from reaction A6 is treated with 2 equivalents of Grignard reagent III, wherein $R^7$ is $R_3Si$ (conditions of reaction B1) followed by tosylation of the resulting alcohol (conditions of reaction A5) and borohydride reduction of the resulting tosylate (conditions of reaction B7) to produce Intermediate 35. The silyl-alcohol protecting groups of this Intermediate are removed (conditions of reaction A2) and the tosylate-sulfonate transformation of the resulting diol performed (conditions of reaction A5) to produce Bis(sulfonoxy)alkyl Pyrazine Compound 36. Pyrazine Compound 37 is produced from Olefinic Sulfonate 13 (R' is H) by its condensation with the carbanion of methyl sulfonic acid methyl ester (conditions of reaction B4) followed by protonation and hydrolysis of the ester group. Alternatively, 37 may be produced by sequential condensation of Aldehyde 4 with 2 equivalents of the carbanion of methyl sulfonic acid methyl ester. After addition of the first equivalent, the resulting hydroxy compound is dehydrated in situ by treatment with acid, yielding 13, in situ, which is then condensed with the second equivalent.

Reactions H4 through H9 show the preparation of Dihydroxy (Sulfonoxy)alkyl Pyrazine compounds 41 and 43. Olefinic Ketone 15 from reaction C2 is converted to Tosylate 38 (reaction H4) through the use of the Scheme B sequence reactions B1, B2 and B3, Ketone 15 being Aldehyde/Ketone II of reaction B1. Tosylate 38 is reduced with an alkali metal borohydride (reaction H5, conditions of reaction B7) to give Silyl Olefin 39. Olefin 39 is converted to Olefinic Sulfonate 40 (reaction H6) by cleavage of the silyl group (conditions of reaction A2) and the tosylate-sulfonate transformation (conditions of reaction A5). Sulfonate 40 is then oxidized (reaction H7) to produce the corresponding Dihydroxy (Sulfonoxy)alkyl Pyrazine Compound 41 by treating it with an olefin oxidizing agent (conditions of reaction C4).

Acetal Ketone 17 is the starting material in reactions H8 and H9 for preparation of Dihydroxy (Sulfonoxy)alkyl Pyrazine Compound 43. Ketone 17 is used as Aldehyde/Ketone II in the Scheme B sequence reaction B6 to produce Olefinic Sulfonate 42. Catalytic reduction of 42 under low hydrogen pressure, using a rhodium chloride, platinium chloride, ruthenium chloride or palladium chloride catalyst and nonpolar solvent such as benzene or hexane followed by acidic hydrolysis of the acetal group will yield Pyrazine Compound 43.

Reactions H10 through H14 illustrate the synthesis of Alkyl (Sulfonoxy)alkyl Pyrazine Compound 46. Aldehyde 4 is converted to Ketone 44 (reaction H10) by an alkyl ($R^9$) Grignard reaction and oxidation of the resulting alcohol (conditions of reactions E4, A3). Ketone 44 is transformed to Tosylate 45a or Olefinic Sulfonate 45b through the use of the Scheme B sequence, Ketone 44 being used as Aldehyde/Ketone II in reactions B1 and B6. Tosylate 45a is then converted to the corresponding Pyrazine Compound 46 (reaction H13) by alkali metal borohydride reduction of the tosylate, cleavage of the silyl protecting group and the tosylate-sulfonate transformation, under conditions as described for reactions B7, A2 and A5. Tosylate 45b is also converted to the corresponding Pyrazine Compound 46 (reaction H14) by catalytic hydrogenation and hydrolysis, as described for reaction H9.

Scheme I depicts the preparation of multifunctional pyrazine compounds having X as a dihydroxyalkyl group of 2 or 3 carbons. Reactions I1 and I2 illustrate the production of bis(dihydroxyalkyl) Pyrazine Compound 48. Olefinic Ketone 15 from reaction C2 is converted to Olefinic Tosylate 47 by use of the Scheme C sequence (reactions C1 and C3), Ketone 15 being used as Aldehyde/ketone II in reaction C1. Alkali metal borohydride reduction of Tosylate 47 (conditions of reaction B7) and olefin oxidation to dihydroxy groups (conditions of reaction C4) produces Pyrazine Compound 48 (reaction I2).

Reactions I3 through I9 illustrate the preparation of (Sulfonoxy)alkyl, Dihydroxyalkyl Pyrazine Compounds 51 and 53. Olefinic Ketone 15 is converted to Tosylate 49 (reaction I3) through the use of the Scheme B sequence, (reactions B1, B2), Ketone 15 being used as Aldehyde/ketone II. Tosylate 49 is then converted to Olefinic Sulfonate 50 (reaction I4) by alkali metal borohydride reduction (conditions of reaction B7) followed by silyl group cleavage (conditions of reaction A2) and the tosylate-sulfonate transformation (conditions of reaction A5). Sulfonate 50 is then oxidized with an olefinic oxidizing agent (reaction I5, conditions of reaction C4) to produce Pyrazine Compound 51. Acetal Ketone 17 can be converted to Pyrazine Compound 53 by using it as Aldehyde/ketone II in the Scheme B sequence (conditions of reaction B6) to produce Olefin Sulfonate 52 which is then catalytically hydrogenated and hydrolyzed (reaction I8, conditions of reaction H9).

Reaction I9 illustrates the preparation of Alkyl, Dihydroxyalkyl Pyrazine Compound 54. Alkyl ($R^9$) Grignard reaction with Olefinic Ketone 15 followed by tosylate formation, tosylate reduction with borohydride and olefin oxidation (conditions of reactions A5, B7 and C4) produces Pyrazine Compound 54.

Scheme J depicts the preparation of pyrazine compounds having X as a (carboxy)alkyl group of 2 to 4 carbons. Reactions J1 through J5 illustrate the preparation of (Sulfonoxy)alkyl, (carboxy)alkyl Pyrazine Compounds 58 and 60. In reactions J1 and J2, Protected Carboxy Ketone 20 is used as Aldehyde/ketone II in the Scheme B sequence (reaction B1) to produce Alcohol 56 which is converted to the methyl ester and used as Alcohol 8 in the Scheme B sequence (tosylate reduction, reactions B3 and B7) to produce Methyl Ester 57. Ester 57 is then converted to Pyrazine Compound 58 by silyl group cleavage (conditions of reaction A2) and tosylate-sulfonate transformation (conditions of reaction A5). Sulfonate and carboxylate esth groups can be converted to salt forms by basic hydrolysis.

In a similar fashion (reactions J4 and J5) Ketone 20 is converted to Pyrazine Compound 60 by using it as Aldehyde/ketone II in the Scheme B sequence (reaction B6) to produce Olefinic Sulfonic Acid 59 which is then hydrolyzed and catalytically hydrogenated (conditions of reaction H9) to yield Compound 60. The ester group can be converted to the salt form by basic hydrolysis.

Reactions J6 and J7 illustrate the preparation of Dihydroxyalkyl, (Carboxy)alkyl Pyrazine Compound 62. Protected Carboxy Ketone 20 is used as Ketone II in the sequence of Scheme C (reaction C1) to produce Olefinic Alcohol 61 which is then deprotected by acidic hydrolysis, tosylated, reduced with alkali metal borohydride (conditions of reactions C3 and C5), and oxidized with an olefinic oxidizing agent (conditions of reaction C4) to produce Pyrazine Compound 62.

Reaction J8 illustrates preparation of Alkyl (Carboxy)alkyl Pyrazine Compound 63. Protected Carboxy Ketone 20 is reacted with an alkyl ($R^9$) Grignard reagent, deprotected by acidic hydrolysis, tosylated and reduced with alkali metal borohydride (conditions of reactions C3 and C5) to produce Pyrazine Compound 63.

Specific syntheses of pyrazine compounds, which rely upon the anionic stabilizion character of the pyrazine nucleus, are shown by Schemes K through M. In these schemes and the discussion hereinafter, the trisubstituted pyrazine nucleus according to the invention, is denoted by the term "Pyr".

Scheme K depicts the preparation of some pyrazine compounds having sulfonic acid group substitutions which utilize nucleophilic reactions. Substitution of a bromomethyl pyrazine with mercaptide anion in polar solvent followed by oxidation with an oxidizing agent such as acidic chromium trioxide or permanganate produces Pyrazinyl Methylsulfonic acid 64 (reaction K1). Direct preparation of the same kind of acid, 1-(Pyrazine-2-yl)alkylsulfonic Acid 65, is achieved by nucleophilic substitution of 2-(1-bromo or iodoalkyl) pyrazine having 1 to 7 carbons in the alkyl group, with sulfite anion in polar solvent followed by acidic work-up, (reaction K2).

Pyrazine stabilization of an in situ generated carbanion is employed in reaction K3 to produce 2-(Pyrazinyl)ethanesulfonic Acid or 2-(Pyrazinyl)-1-(alkyl)ethysulfonic acid 66 by condensation of 2-(1-alkenyl) pyrazine with sulfite anion in polar solvent followed by acid work-up.

Condensation of a cyclic sultone having 3 to 6 methylenes with pyrazinylmethyl sodium, which is generated in situ from methylpyrazine and sodium amide in ammonia, will produce Omega-(pyrazinyl)alkylsulfonic Acid 67 having 3 to 6 carbons in the alkyl group, (reaction K4).

Finally, nucleophilic substitution on the pyrazine nucleus of chloro or bromopyrazine using sulfite anion in water generates Pyrazine Sulfonic Acid 68 after acid work-up, (reaction K5).

Scheme L depicts the preparation of hydroxyalkyl pyrazine compounds. Several methods are employed for these preparations. Under the conditions of reaction C4, olefinic oxidation of (but-1-en-4-yl)pyrazine, produced by condensation of alkyl bromide and pyrazinylmethyl sodium, produces (3,4-Dihydroxybutyl)pyrazine 69, (reaction L1). Condensation of methyl pyrazine with paraformaldehyde will produce 2-(2-Hydroxyethyl)pyrazine 70 (reaction L2) or its condensation with an alkyl aldehyde in base will produce 2-(2-alky-2-hydroxyethyl)pyrazine (reaction L3). Similarly, condensation of the base generated anion of methyl pyrazine with an ester of an alkylcarboxylic acid having 1 to 6 carbons in the alkyl group will produce Ketone Intermediate 72 which can be reduced with sodium borohydride or a similar hydride reducing agent to produce Pyrazine 71, (reaction L4).

Nucleophilic substitution of (1-bromoalkyl)pyrazine with hydroxide will produce (1-Hydroxyalkyl)pyrazine 73 (reaction L5). Hydroxymethylpyrazine 74 can be prepared from methylpyrazine by hydrogen peroxide oxidation followed by treatment with an organic acid anhydride and hydrolysis with base, (reaction L6).

Scheme M depicts a specific synthesis of a pyrazinyl propionic acid. Methylpyrazine anion is condensed with trichloroacetaldehyde followed by treatment with base (hydroxide), then acidification to produce 3-(-Pyrazinyl) Acrylic Acid 75. This acid is then catalytically hydrogenated over palladium on charcoal to yield 3-(2-Pyrazinyl)propionic Acid 76.

Scheme N illustrates the second phase of the overall synthetic plan, monoquaternization. In general, when the quaternizing group is alkyl, the corresponding alkyl bromide or iodide is reacted with the appropriate pyrazine compound to quaternize a pyrazine nucleus, (reaction N1). When the pyrazine compound is monosubstituted at $R^3$, this process will result in quaternization of the nitrogen in the meta position relative to $R^3$. For other substitution patterns, steric control will determine the pyrazine nitrogen that is quaternized. Consequently, when there are a number of substituents present, e.g., $R^2$, $R^3$, $R^4$ and $R^5$, mixtures can be produced which are separable by column chromatography, high pressure chromatography or a similar technique.

When the monoquaternizing group is also functionalized with a carboxyl or sulfonoxy group, the corresponding pyrazinium compound can be produced as illustrated by reactions N2 through N5. Condensation of the appropriate pyrazine compound with methylvinylsulfonate or acrylic acid will produce the corresponding 1-(2-Sulfonoxyethyl)pyrazinium Compound 78 or 1-(2-Carboxyethyl)pyrazinium hydrobromide Compound 80, (reactions N2 and N4). Likewise, condensation of the appropriate pyrazine compound with a sultone of 3 to 6 carbons will produce the corresponding 1-(omega-Sulfonoxyalkyl)pyrazinium Compound 79, (reaction N3). Finally, condensation of methyl omega-iodoalkylsulfonate or carboxylate having 1 to 3 carbons in the alkyl group, with the appropriate pyrazine compound will produce, after hydrolysis of the ester group, 1-[Omega-(sulfonoxy or carboxy)alkyl] Pyrazinium Compound 81, (reaction N5).

Isolation, purification and work-up of the pyrazine intermediates, pyrazine compounds and pyrazinium compounds described for Schemes A through N can be accomplished by generally known methods. These include neutralization with appropriate acids or bases, aqueous-organic solvent extraction, partition and gel permeation column chromatography on such materials as silica gel, polyamide, polyacrylamide, ion exchange resin, cross-linked-swelled dextrin gel (Sephadex), celite and the like, high pressure liquid chromatography using any of the known stationary supports, crystallization, vacuum distillation, sublimation, etc. Furthermore, where appropriate, dry conditions and solvents will be employed.

Scheme A
Synthesis of Synthon 4 And Monofunctional Products

A1. 1

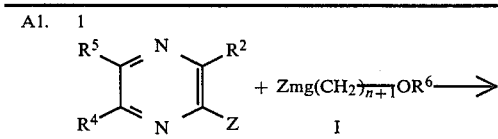

$+ Zmg(CH_2)_{n+1}OR^6 \longrightarrow$

I

-continued

Scheme A
Synthesis of Synthon 4 And Monofunctional Products

2 $HetCH_2OR^6$

A2. $2 + HOAc/H_2O$ ($R^6$ is THP) $\longrightarrow$ 3 $HetCH_2OH$
$Bu_4NF$ ($R^6$ is $SiR_3$)

A3. $3 + $ oxidation $\longrightarrow$ 4 HetCHO

A4. $3 + $ oxidation $\longrightarrow$ 5 $HetCO_2H$

A5. $3 + $ 1.TsCl, $2.Na_2SO_3 \longrightarrow$ 6 $HetCH_2SO_3E$

A6. $5 + R^9OH$, acid $\longrightarrow$ 7 $HetCH_2CO_2R^9$

Notations:

1. 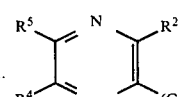 is Het wherein n is an integer from 1 to 6.
2. Z is Cl, Br.
3. $R^6$ is THP, $SiR_3$.
4. E is an alkali metal or alkaline earth metal cation.
5. $R^9$ is alkyl of 1 to 3 carbons.

Scheme B
Sequence For Preparation of
Intermediates Leading To A
Sulfonic Acid Group B1. $HetCOR' + ZMg(CH_2)_kOR^7 \longrightarrow$
    II       III 8 $HetCR'OH(CH_2)_kOR^7$ B2. 8 (R' is H) + oxidation $\longrightarrow$ 9 $HetCO(CH_2)_4OR^7$ B3. 8 + TsCl $\longrightarrow$ 10 $HetCR'OTs(CH_2)_4OR^7$ B4. II + $1.CH_3SO_3Me/NaH \longrightarrow$
    $2.R_3SiCl$ 11 $HetCR'(OSiR_3)CH_2SO_3Me$ B5. 11 (R' is H) + $1.Bu_4NF \longrightarrow$ 12 $HetCOCH_2SO_3Me$
    2.oxid.

B6. II + $Ph_3PCHSO_3Me \longrightarrow$ 13 $HetCR'=CHSO_3Me$
    IV

B7. 10 + $NaBH_4 \longrightarrow$ 10-B $HetCHR'(CH_2)_kOR^7$

Notations:
1. R' is hydrogen or another functional group according to the invention.
2. k is an integer from 2 to 3.
3. $R^7$ is THP, $SiR_3$.

| Scheme C |
| --- |
| Sequence For Preparation Of Intermediates Leading To A Dihydroxyalkyl Group Of 2-3 Carbons |

C1. $\text{II} + \text{LiCH}=\text{CHR}^8$ 
or
$\text{ZMgCH}_2\text{CH}=\text{CH}_2$
$\quad\quad\quad\quad\quad\quad$ V
$\longrightarrow$ 14 $\text{HetCR'OH(CH}_2)_l\text{CH}=\text{CHR}^8$ C2. 14 (R' is H) + oxid. $\longrightarrow$ 15 $\text{HetCO(CH}_2)_l\text{CH}=\text{CHR}^8$ C3. 14 + TsCl $\longrightarrow$ 16 $\text{HetCR'OTs(CH}_2)_l\text{CH}=\text{CHR}^8$ C4. 15 + olefin oxid. $\longrightarrow$ 15C $\text{HetCO(CH}_2)_l\text{CHOHCHOHR}^8$ 15C + acetone, acid $\longrightarrow$ 17 $\text{HetCO(CH}_2)_l\text{CHCHR}^8$
$\quad\quad\quad\quad\quad\quad\quad\quad\quad\quad\quad\quad\quad\quad\quad\quad$ O  O
$\quad\quad\quad\quad\quad\quad\quad\quad\quad\quad\quad\quad\quad\quad\quad\quad\quad$ \\/
$\quad\quad\quad\quad\quad\quad\quad\quad\quad\quad\quad\quad\quad\quad\quad\quad\quad$ X C5. 16 + $\text{NaBH}_4$ $\longrightarrow$ 16C $\text{HetCHR'(CH}_2)_l\text{CH}=\text{CHR}^8$ Notations:
1. $R^8$ is H, Me.
2. $l$ is 0, 1.

| Scheme D |
| --- |
| Sequence For Preparation Of Intermediates Leading To A Carboxylic Acid Group of 2-4 Carbons |

D1. $\text{II} + \text{ZMg(CH}_2)_m\text{Oxaz}$ $\longrightarrow$ 18 $\text{HetCR'OH(CH}_2)_m\text{Oxaz}$
$\quad\quad\quad\quad\quad\quad\quad$ VI D2. 18 + 1.MeOH/HCl, 2.TsCl $\longrightarrow$
3.$\text{NaBH}_4$
19 $\text{HetCHR'(CH}_2)_m\text{CO}_2\text{Me}$ D3. 18 (R' is H) + oxid. $\longrightarrow$ 20 $\text{HetCO(CH}_2)_m\text{Oxaz}$ Notation:
1. 
$$\begin{array}{c} \quad\quad O \\ \diagup\!\!\!\diagdown\!\!\!\diagup\!\!\!\diagdown \\ \quad\quad N \end{array} \text{ is Oxaz}$$
2. m is 1-3.

| Scheme E |
| --- |
| Synthesis Of Pyrazine Compounds Having X As Hydroxy |

E1. 8 ($R^7$ is THP) + 1. $R_3\text{SiCl}$ $\longrightarrow$ 21 $\text{HetCHOSiR}_3(\text{CH}_2)_k\text{SO}_3\text{E}$
2. Scheme A(A2, A5)

E2. 21 and 11 (R' is H) + $\text{Bu}_4\text{NF}$ $\longrightarrow$ 22 $\text{HetCHOH(CH}_2)_m\text{SO}_3\text{E}$ E3. 14(R' is H) + Scheme C $\longrightarrow$
23 $\text{HetCHOH(CH}_2)_l\text{CHOHCHR}^8\text{OH}$ -continued

| Scheme E |
| --- |
| Synthesis Of Pyrazine Compounds Having X As Hydroxy |

E4. 4 + 1. $R^9\text{MgZ}$, 2. acid $\longrightarrow$ 24 $\text{HetCHOHR}^9$

| Scheme F |
| --- |
| Synthesis Of Pyrazine Compounds Having X As Carboxyl |

F1. 10 (R' is H) + KCN $\longrightarrow$ 25a $\text{HetCH(CN)(CH}_2)_k\text{OSiR}_3$
($R^7$ is $\text{SiR}_3$)

F2. 13 + KCN $\longrightarrow$ 25b $\text{HetCH(CN)CH}_2\text{SO}_3\text{Me}$

F3. 25a + Scheme A(A2, A5) $\longrightarrow$ 25c $\text{HetCH(CN)(CH}_2)_k\text{SO}_3\text{E}$ F4. 25b and 25c + hydrol. $\longrightarrow$ 26 $\text{HetCH(CO}_2\text{H)(CH}_2)_m\text{SO}_3\text{E}$ F5. 15 + 1. $\text{Ph}_3\text{PCBr}_2$, 2. NaOMe $\longrightarrow$ 27 $\text{HetCH(CH}_2)_l\text{CH}=\text{CHR}^8$
$\quad\quad$ VII $\quad\quad$ 3. MeOH/HCl $\quad\quad\quad\quad\quad\quad\quad\quad\quad$ |
$\quad\quad\quad\quad\quad\quad\quad\quad\quad\quad\quad\quad\quad\quad\quad\quad\quad\quad\quad\quad$ $\text{CO}_2\text{Me}$ F6. 27 + Scheme C(C4) $\longrightarrow$
28 $\text{HetCH(CO}_2\text{H)(CH}_2)_l\text{CHOHCHR}^8\text{OH}$ F7. 4 + 1. $R^9\text{MgZ}$ 2. TsCl $\longrightarrow$ 29 $\text{HetCHR}^9\text{CO}_2\text{E}$
3. KCN $\quad$ 4. Acid

| Scheme G |
| --- |
| Synthesis Of Pyrazine Compounds Having X As A Sulfonoxy Group |

G1. 8(R' is H) + 1. acid $\longrightarrow$ 30 $\text{HetCHOTs(CH}_2)_k\text{OTs}$
2. TsCl G2. 30 and 13 + Scheme A(A5) $\longrightarrow$ 31 $\text{HetCH(SO}_3\text{E)(CH}_2)_m\text{SO}_3\text{E}$ G3. 16(R'=H) + Sch. A(A5) $\longrightarrow$ 32 $\text{HetCH(SO}_3\text{E)(CH}_2)\text{CH}=\text{CHR}^8$ G4. 32 + Scheme C(C4) $\longrightarrow$
33 $\text{HetCH(SO}_3\text{E)(CH}_2)_l\text{CHOHCHR}^8\text{OH}$ G5. 4 + 1. $R^9\text{MgZ}$ $\longrightarrow$ 34 $\text{HetCHR}^9\text{SO}_3\text{E}$
2. Scheme A(A5)

| Scheme H |
| --- |
| Synthesis Of Pyrazine Compounds Having X As A (Sulfonoxy) Alkyl Group Of 2-3 Carbons |

H1. 7 + 1. 2M of III $\longrightarrow$ 35 $\text{HetCH[(CH}_2)_k\text{OSiR}_3]_2$
2. Scheme B(B3, B7)

H2. 35 + Scheme A(A2, A5) $\longrightarrow$ 36 $\text{HetCH[(CH}_2)_k\text{SO}_3\text{E}]_2$ 13 (R' is H) + 1. $\text{CH}_3\text{SO}_3\text{Me/NaH}$ $\longrightarrow$ 37 $\text{HetCH[CH}_2\text{SO}_3\text{E]}_2$
2. hydrolysis -continued
Scheme H
Synthesis Of Pyrazine Compounds
Having X As A (Sulfonoxy) Alkyl
Group Of 2-3 Carbons H4. 15 + Scheme B(B1) → 38 HetCOTs(CH$_2$)$_k$OSiR$_3$
            |
            (CH$_2$)$_l$CH=CHR$^8$ H5. 38 + Scheme B(B7) → 39 HetCH(CH$_2$)$_k$OSiR$_3$
            |
            (CH$_2$)$_l$CH=CHR$^8$ H6. 39 + Scheme A(A2, A5) → 40 HetCH(CH$_2$)$_k$SO$_3$E
            |
            (CH$_2$)$_l$CH=CHR$^8$ H7. 40 + Scheme C(C4) → 41 HetCH(CH$_2$)$_k$SO$_3$E
            |
            (CH$_2$)$_l$CHOHCHR$^8$OH H8. 17 + Scheme B(B6) → 42 HetC=CHSO$_3$Me
            |
            (CH$_2$)$_l$CH  CHR$^8$
                    |   |
                    O   O
                     \\ /
                      X H9. 42 + 1. H$_2$/catalyst → 43 HetCHCH$_2$SO$_3$E
       2. acid           |
                         (CH$_2$)$_l$CHOHCHR$^8$OH H10. 4 + 1. R$^9$MgZ → 44 HetCOR$^9$
        2. oxid.

H11. 44 + Scheme B(B1, B3) → 45a HetCR$^9$OTs(CH$_2$)$_k$OSiR$_3$

H12. 44 + Scheme B(B6) → 45b HetCR$^9$=CHSO$_3$Me

H13.
H14. ⎡ 45a + Scheme B(B7)     ⎤
     ⎢ Scheme A(A2, A5)        ⎥ → 46 HetCHR$^9$(CH$_2$)$_m$SO$_3$E
     ⎣ 45b + 1. H$_2$/catalyst ⎦
            2. acid Scheme I
Synthesis Of Pyrazine Compounds
having X As A Dihydroxyalkyl
Group Of 2-3 Carbons I1. 15 + Scheme C(C1, C3) → HetCOTs[(CH$_2$)$_l$CH=CHR$^8$]$_2$ I2. 47 + Scheme C(C5, C4) → HetCH[(CH$_2$)$_l$CHOHCHR$^8$OH]$_2$ I3. 15 + Scheme B(B1, B3) → HetCOTs(CH$_2$)$_k$OSiR$_3$
            |
            (CH$_2$)$_k$CH=CHR$^8$ I4. 49 + Scheme B(B7) → 50 HetCH(CH$_2$)$_k$SO$_3$E
     Scheme A(A2, A5)    |
                         (CH$_2$)$_l$CH=CHR$^8$ I5. 50 + Scheme C(D4) → 51 HetCH(CH$_2$)$_k$SO$_3$E
            |
            (CH$_2$)$_l$CHOHCHR$^3$OH I6. 17 + Scheme B(B6) → 52 HetC=CHSO$_3$Me
            |
            (CH$_2$)$_l$CHCHR$^8$ -continued
Scheme I
Synthesis Of Pyrazine Compounds
having X As A Dihydroxyalkyl
Group Of 2-3 Carbons I7. 52 + Scheme H(H9) → 53 HetCHCH$_2$SO$_3$E
            |
            (CH$_2$)$_l$CHOHCHR$^8$OH I8. 15 + R$^9$MgZ → 54 HetCHR$^9$(CH$_2$)$_l$CHOHCHR$^8$OH
     Scheme C(C3, C5, C4)

Scheme J
Synthesis Of Pyrazine Compounds
Having X as A (Carboxy)alkyl
Group of 2-4 Carbons J1. 20 + Scheme B(B1) → 56 HetCOH(CH$_2$)$_k$OSiR$_3$
            |
            (CH$_2$)$_m$Oxaz J2. 56 + 1.MeOH/HCl → 57 HetCH(CH$_2$)$_k$OSiR$_3$
      2.Scheme B(B3,B7)    |
                           (CH$_2$)$_m$CO$_2$Me J3. 57 + Scheme A(A2,A5) → 58 HetCH(CH$_2$)$_k$SO$_3$E
            |
            (CH$_2$)$_m$CO$_2$E J4. 20 + Scheme B(B6) → 59 HetC=CHSO$_3$Me
            |
            (CH$_2$)$_m$Oxaz J5. 59 + MeOH/HCl, Scheme H(H9) → 60 HetCHCH$_2$SO$_3$E
            |
            (CH$_2$)$_m$CO$_2$E J6. 20 + Scheme C(C1) → 61 HetCOH(CH$_2$)$_l$CH=CHR$^8$
            |
            (CH$_2$)$_m$Oxaz J7. 61 + MeOH/HCl → 62 HetCH(CH$_2$)$_l$CHOHCHR$^8$OH
     Scheme C(C3,C5,C4)    |
                           (CH$_2$)$_m$CO$_2$E J8. 20 + 1.R$^9$MgZ, 2.MeOH/HCl → 63 HetCHR$^9$(CH$_2$)$_m$CO$_2$E
        3.Scheme B(B3,B7)

Scheme K
Specific Synthesis Of
Pyrazine Sulfonic Acids

K1. PyrCH$_2$Br + 1.NaSH → 64 PyrCH$_2$SO$_3$E
              2.K MnO$_4$

K2. Pyr CHR$^{10}$Br + Na$_2$SO$_3$/acid → 65 PyrCHRSO$_3$E
    R$^{10}$ is alkyl of 1-6 carbons,
    hydrogen K3. PyrCH=CHR$^{10}$ + Na$_2$SO$_3$ → 66 PyrCH$_2$CHR$^{10}$SO$_3$E K4. PyrCH$_3$ + (CH$_2$)$_n$SO$_3$ → 67 PyrCH$_2$(CH$_2$)$_n$SO$_3$E -continued
Scheme K
Specific Synthesis Of Pyrazine Sulfonic Acids

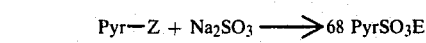

Notation: 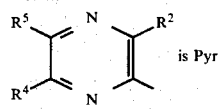 is Pyr

Scheme L
Specific Synthesis Of Pyrazine Alcohols

L1. 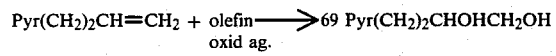

L2. 

L3. 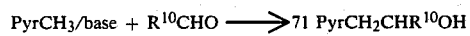

L4. 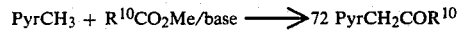

L5. 

L6. 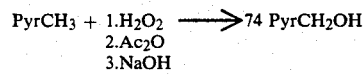

Scheme M
Specific Synthesis Of Pyrazine Carboxylic Acids

M1. 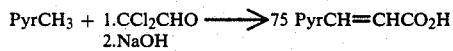

Scheme N
Synthesis of Monoquaternized Pyrazinium Compounds

N1. 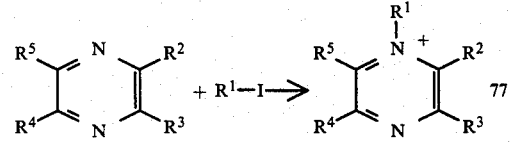

N2. 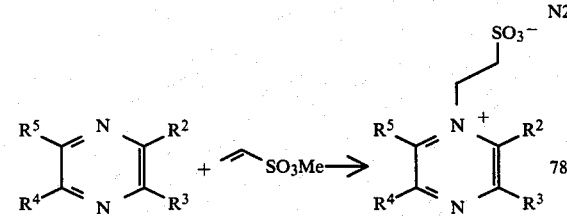

-continued
Scheme N
Synthesis of Monoquaternized Pyrazinium Compounds

N3. 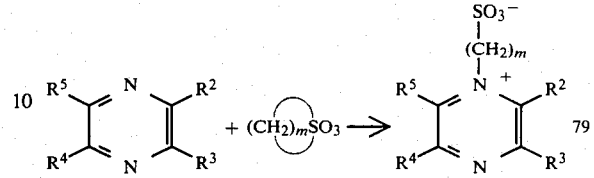

N4. 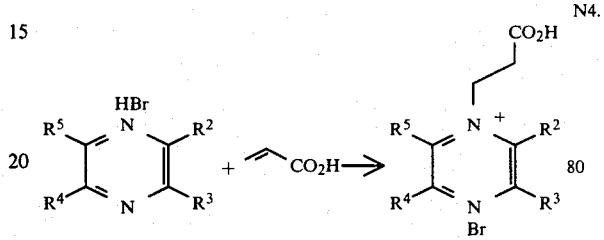

N5. 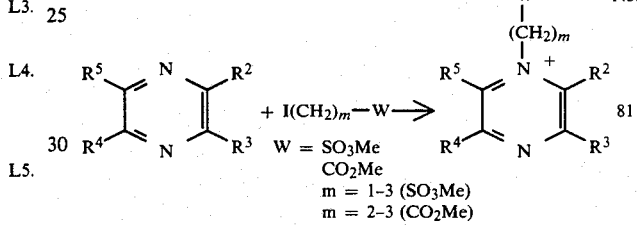

W = SO$_3$Me
CO$_2$Me
m = 1–3 (SO$_3$Me)
m = 2–3 (CO$_2$Me)

The pyrazinium compounds of the invention are useful as electron carriers in photolytic systems. They can transfer "high energy" electrons from a photo-activating source to a catalyst which would employ the high energy electrons in a reductive reaction with water or nitrogen. Accordingly, they are useful in the production of ammonia, hydrogen and oxygen.

The pyrazinium compounds are also useful as vectors for the stimulation of ammonia production by nitrogen fixing bacteria associated with legumes. They can take part in the metabolic processes of the bacteria and efficiently transfer energy from the host to the mitochondria thus facilitating their nitrogen fixation.

In general, it will be found that an in vitro photolytic system of chloroplasts, pyrazinium compound, appropriate solvent such as water, and catalyst such as nitrogenase contained in a suitable system for isolating gaseous products, preventing reductive short-circuiting and minimizing atmospheric interference can function as a hydrogen or ammonia production system. The chloroplasts may be isolated from appropriate plant sources such as spinach or chenopodium leaves and will be contained in a vessel which permits their absorption of the appropriate light wavelengths. This kind of system is preferred, however, it is also possible to employ synthetic material which is light sensitive and will generate photoexcited electrons. Such examples would include ruthenium, molybdenum or iron coordination complexes such as bipyridyl, porphyrin complexes, see Kirsh, et al., *Helv. Chim Acta*, 62, 1345(1979).

In the preferred method, a suitable system may be designed around nitrogenase catalyst and chloroplasts discussed in the literature, see for example M. Calvin in "Living Systems As Energy Converters", North Holland Publishing, Amsterdam, 1977, pp. 231-259; Seibert, et al., *Sol. Energy Res. Inst.* (Tech. Rep.) SERI/JP-33-410(1979); Benemann, et al., *Enzyme Microb. Technol.*, 2, 103(1980); and L. O. Krampitz, NSF-RANN Report NO. HA2 N-73-014. Although a one stage system can be used, a two stage system is preferred. In this system, chloroplasts, water and pyrazinium compound may be placed in a glass vessel equipped with a water inlet and cooling. Into this aqueous mixture can then be placed a smaller vessel with a top opening and a bottom or side opening covered with a semipermeable membrane such as cellulose or another dialysis material capable of allowing passage of small but not large molecular weight molecules. The smaller vessel may contain an aqueous mixture of reductive catalyst such as nitrogenase and the pyrazinium compound. The top opening can be fitted with gas inlet and outlet tubes which prevent direct atmospheric interference with the aqueous reductive catalyst mixture and allow application of the appropriate reactant gases. The tubes can also carry the gaseous product to storage. Application of light will initiate the chloroplast photolytic reaction and produce reduced pyrazinium compound. Diffusion of the reduced compound across the membrane barrier can initiate catalytic production of the appropriate product, hydrogen if there is no nitrogen or carbon dioxide present, otherwise ammonia.

A high rate of diffusion of the electron carrier through the membrane is believed to be important since it may favor efficient coupling with the enzyme. Also, it may be advantageous to add ferredoxin to the enzyme phase which can serve as an intermediate coupling agent. It is believed that intimate and fast coupling of the chlorophyll and enzyme through the carrier transfer mechanism may be a factor for the efficiency of the two phase system.

The low molecular weight and small size of the pyrazinium compounds of the invention permit practical use of the two stage system. Known semipermeable membranes can be used whereas with protein electron carriers such as ferredoxin, such membranes will prevent carrier passage. Moreover, the ability to produce large quantities of the pyrazinium compounds permits economical use of large systems.

The activity of the pyrazinium compounds as electron carriers in an illuminated photocouple process using isolated chloroplasts and the reductive enzyme catalyst nitrogenease has been determined using the bioassay of Benemann, et al., *Proc. Natl. Acad. Sci. USA*, 64, 1079(1969). In this method, the carrier activity is measured as a function of nitrogenase reduction of acetylene to ethylene, the rate of production of ethylene being the direct measurement.

For the bioassay, the nitrogenase sample was prepared from a culture of *Azotobacter vinelandii* grown to a cell density of about 1 g/l. The cells harvested by centrifugation were broken in a French press, cell debris spun off at 10,000 XG for 1 hr., and the supernatant containing 40 mg/ml protein was used in the bioassay experiments. Heat-inactivated chloroplasts from spinach leaves as described by Benemann were also used. The synthetic carriers were tested in aqueous solutions at concentrations of 2 mM, while the standard, clostridial ferredoxin, was used in 0.2 mM aqueous solution. The concentrations of carriers in the assay mixtures were chosen so as to guarantee carrier saturation conditions. Thus, the observed differences in rates of ethylene production from the substrate acetylene were assigned directly to variations in the efficiency of electron transfer from the illuminated chloroplast to the nitrogenase. The results obtained for acetylene reduction (nitrogen fixation) using the pyrazinium compounds of Examples 1 through 42 are summarized in Table I and are expressed as nmoles of ethylene produced per mg protein per minute. These results also show the limits of activity as a function of pyrazinium compound chemical structure.

It has been reported that the nitrogenase system is made up of two dissociating protein components, neither of which has activity by itself, L. E. Mortenson, et al., *Ann. Rev. Biochem.*, 48, 387(1979). The first is the so called iron protein, that has a molecular weight of 57,000, four atoms of iron and four acid-labile sulfur atoms arranged in one iron-sulfur cluster. The second component, the molybdenum-iron protein, is much more complex than the iron protein. It has a molecular weight of about 240,000, and contains two molybdenum, 28-32 iron, and about 28 acid-labile sulfur atoms. The electrons are donated by the reduced forms of adequate electron carriers (such ferredoxins and flavodoxins in in vivo systems) to the iron protein, in a one-electron reduction process that consumes two mols of adenosine triphosphate per one F (1 faraday=one mole of electrons=96,493 coulombs) transferred. Electrons are then transferred intramolecularly from the iron protein to the molybdenium-iron protein, that acts as a storage sink of electrons and passes them to the substrates in multiples of two.

The natural electron carriers for the nitrogenase have midpoint potentials ranging from $-495$ mV for *Azotobacter vinelandii* flavodoxin, to $-570$ mV for *Clostridium pasteurianum* ferredoxin, but little else is known about the actual redox potentials needed for optimal operation of the nitrogenase. A redox titration of *Azotobacter vinelandii* nitrogenase with the couple $SO_2^{-}/SO_3^{=}$ has shown that the iron protein suffers a one-electron reduction at a midpoint potential of $-413$ mV at pH 7.0, A. Braaksma, et. al., *Eur. J. Biochem.*, 121, 483 (1982).

Highly purified preparations of the nitrogenase have shown specific activities of 3000 nmol $C_2H_4$ formed/mg protein/min, A. Braaksma, et. al., *Eur. J. Biochem.*, 121, 483 (1982), using sodium dithionite as reductant. The crude nitrogenase preparations used in the present study gave, under similar conditions, 67 nmol $C_2H_4$/mg protein/min. This value corresponds to a content of 2.2% nitrogenase on protein basis.

It has been recognized for sometime the connection existing between hydrogen metabolism and nitrogen fixation. Biosystems under active nitrogen fixation were observed to evolve hydrogen and hydrogen was observed to be inhibitory to nitrogen fixation. When nitrogenase was purified extensively, as mentioned above, it became apparent that in addition to nitrogen, nitrogenase also catalyzed the reduction of protons. The evolution of hydrogen is particularly active in the absence of the normal substrates for nitrogenase (nitrogen, acetylene, cyanide, azide, etc.), and is dependent upon a strong reductant and adenosine triphosphate hydrolysis. Since hydrogen evolution is not inhibited by CO, but reduction of nitrogen and other substrates is, the reduction of protons presumably occurs at a site other than the site of nitrogen reduction, H. C. Winter, et. al., *Ann Rev. Biochem*, 45, 409 (1976). Accordingly, with the same bioassay system and with exclusion of nitrogen, and acetylene, the activity of the pyrazinium compounds to act as carriers for production of hydrogen has been determined.

The results of this study, which are summarized in Table II, indicate that the pyrazinium salts that mediate the reduction of acetylene with electrons from the photoexcited chloroplast, are also mediating the reduction of protons by the nitrogenase.

The ranking of the pyrazinium salts for both activities, relative to the activity of ferredoxin, are compared in Table III. The data suggest that the nitrogenase exhibits stricter structural selectivity for the carriers in the presence of substrate (acetylene) than in the absence of it. It can be seen, however, that a substantial equivalence in the structure/activity relationships exists for both processes. For example, out of the ten most active pyrazines in the reduction of acetylene, seven also rank within the ten most active for evolution of hydrogen.

In a thermodynamical sense, a functional carrier for the system under consideration must operate between an upper limit of redox potential set by the negative potential of the illuminated chloroplast ($-610$ mV), and a lower energy level corresponding to the redox potential of the adenosine triphosphate-activated iron protein, found to be $-473$ mV. This is the case for the clostridial ferredoxin, that operates with a half-wave potential of $-570$ mV at pH 7.52, Chien, *J. Pharm. Sci.*, 65, 1471(1976). Therefore, it was of interest to measure polarographically the half-wave potentials of the several pyrazinium salts under consideration, to determine the possible effect of structure upon their redox potentials. Previous polarographic studies, L. Roullier, et. al., *Electrochimica Acta*, 25, 795 (1980), have shown that monoquaternary pyrazines are reduced in two waves of 1F. The first wave corresponds to a one-electron reduction and yields a relatively stable radical, which is reduced in the second wave to the dihydropyrazine (two-electron reduction product). Most of the pyrazinium salts studied exhibited a two-wave profile, although some of them have shown only one wave.

Table IV lists the half-wave potentials (E1/2 vs. SCE) for the first wave reduction, measured polarographically in 0.1 M phosphate buffer pH 7.55, at 25° C., for the pyrazinium salts ranked according to their activity in the acetylene reduction bioassay. Based upon these data it can be said that no apparent correlation exists between redox potentials and cofactor activity for the nitrogenase. It is likely that the differences in bioactivity among the pyrazinium salts studies probably correspond to chemical structure variations affecting the cofactor/enzyme interaction and binding.

TABLE I

Electron Carrier Activities towards Nitrogenase of Synthetic Pyrazinium Compounds, Measured by the Chloroplast-coupled Reduction of Acetylene to Ethylene.

| ELECTRON CARRIER COMPOUND NO. | ACTIVITY (nmoles $C_2H_4$/mg protein/min) | ACTIVITY RELATIVE TO FERREDOXIN (%) |
|---|---|---|
| Clostridial Ferredoxin | 13.5 | 100 |
| 700 | 14.0 | 104 |
| 400 | 3.5 | 26 |
| 500 | 3.0 | 22 |
| 300 | 5.5 | 41 |
| 200 | 2.3 | 17 |
| 2600 | 13.2 | 98 |
| 2400 | 14.2 | 105 |
| 3000 | 13.4 | 99 |
| 3200 | 13.3 | 98 |
| 2000 | 8.3 | 61 |
| 2800 | 8.3 | 61 |
| 600 | 8.7 | 64 |

TABLE I-continued

Electron Carrier Activities towards Nitrogenase of Synthetic Pyrazinium Compounds, Measured by the Chloroplast-coupled Reduction of Acetylene to Ethylene.

| ELECTRON CARRIER COMPOUND NO. | ACTIVITY (nmoles $C_2H_4$/mg protein/min) | ACTIVITY RELATIVE TO FERREDOXIN (%) |
|---|---|---|
| 1200 | 14.5 | 107 |
| 800 | 6.8 | 50 |
| 2200 | 7.5 | 55 |
| 3400 | 2.7 | 20 |
| 3500 | 0.7 | 5 |
| 1700 | 4.5 | 33 |
| 3700 | 4.2 | 31 |
| 1000 | 12.8 | 95 |
| 4200 | 0.1 | 1 |
| 4100 | 14.8 | 110 |
| 1500 | 5.5 | 41 |
| 1801 | 10.7 | 79 |
| 1800 | 16.7 | 124 |
| 3901 | 3.0 | 22 |
| 3900 | 3.7 | 27 |
| 4000 | 3.8 | 28 |
| 3800 | 2.0 | 15 |
| 4300 | 0.7 | 5 |
| 4400 | 0.0 | 0 |
| 4500 | 0.0 | 0 |
| 4600 | 0.0 | 0 |
| 4700 | 0.7 | 5 |
| 4800 | 0.2 | 1 |
| 4900 | 0.3 | 2 |
| 5000 | 0.0 | 0 |
| 5100 | 1.8 | 13 |
| 5200 | 0.0 | 0 |

TABLE II

Electron Carrier Activities for Nitrogenase of Synthetic Pyrazinium Compounds, Measured by the Chloroplast-coupled Evolution of Hydrogen, in the Absence of Substrate.

| ELECTRON CARRIER COMPOUND NO. | ACTIVITY (nmoles $H_2$/mg protein/min) | ACTIVITY RELATIVE TO FERREDOXIN (%) |
|---|---|---|
| Clostridial Ferredoxin | 26.7 | 100 |
| 700 | 19.7 | 74 |
| 400 | 19.7 | 74 |
| 500 | 12.3 | 46 |
| 300 | 8.1 | 30 |
| 200 | 17.2 | 64 |
| 2600 | 41.2 | 154 |
| 2400 | 34.1 | 128 |
| 3000 | 33.1 | 124 |
| 3200 | 43.1 | 161 |
| 2000 | 26.6 | 100 |
| 2800 | 37.3 | 140 |
| 600 | 28.4 | 106 |
| 1200 | 38.1 | 143 |
| 800 | 7.5 | 28 |
| 2200 | 26.2 | 98 |
| 3400 | 29.7 | 111 |
| 3500 | 5.0 | 19 |
| 1700 | 16.6 | 62 |
| 3700 | 8.6 | 32 |
| 1000 | 19.5 | 73 |
| 4200 | 1.6 | 6 |
| 4100 | 19.4 | 73 |
| 1500 | 22.9 | 86 |
| 1801 | 28.4 | 106 |
| 1800 | 34.4 | 129 |
| 3901 | 6.9 | 26 |
| 3900 | 11.9 | 45 |
| 4000 | 9.5 | 36 |
| 3800 | 5.8 | 22 |
| 4300 | 3.7 | 14 |
| 4400 | 0.0 | 0 |
| 4500 | 0.0 | 0 |
| 4600 | 0.0 | 0 |
| 4700 | 1.4 | 5 |
| 4800 | 1.4 | 5 |
| 4900 | 2.2 | 8 |
| 5000 | 0.0 | 0 |

TABLE II-continued

Electron Carrier Activities for Nitrogenase of Synthetic Pyrazinium Compounds, Measured by the Chloroplast-coupled Evolution of Hydrogen, in the Absence of Substrate.

| ELECTRON CARRIER COMPOUND NO. | ACTIVITY (nmoles $H_2$/mg protein/min) | ACTIVITY RELATIVE TO FERREDOXIN (%) |
|---|---|---|
| 5100 | 2.8 | 10 |
| 5200 | 0.0 | 0 |

TABLE III

Ranking of Synthetic Pyrazinium Compounds According to their Electron Carrier Activities Towards Nitrogenase, Expressed as Percent Activity Relative to Clostridial Ferredoxin.

| ETHYLENE FORMATION | | HYDROGEN EVOLUTION | |
|---|---|---|---|
| Compound No. | % Ferredoxin Activity | Compound | % Ferredoxin Activity |
| 1800 | 124 | 3200 | 161 |
| 4100 | 110 | 2600 | 154 |
| 1200 | 107 | 1200 | 143 |
| 2400 | 105 | 2800 | 140 |
| 700 | 104 | 1800 | 129 |
| Ferredoxin | 100 | 2400 | 128 |
| 3000 | 99 | 3000 | 124 |
| 2600 | 98 | 3400 | 111 |
| 3200 | 98 | 600 | 106 |
| 1000 | 95 | 1801 | 106 |
| 1801 | 79 | 2000 | 100 |
| 600 | 64 | Ferredoxin | 100 |
| 2000 | 61 | 2200 | 98 |
| 2800 | 61 | 1500 | 86 |
| 2200 | 55 | 700 | 74 |
| 800 | 50 | 400 | 74 |
| 300 | 41 | 1000 | 73 |
| 1500 | 41 | 4100 | 73 |
| 1700 | 33 | 200 | 64 |
| 3700 | 31 | 1700 | 62 |
| 4000 | 28 | 500 | 46 |
| 3900 | 27 | 3900 | 45 |
| 400 | 26 | 4000 | 36 |
| 500 | 22 | 3700 | 32 |
| 3901 | 22 | 300 | 30 |
| 3400 | 20 | 800 | 28 |
| 200 | 17 | 3901 | 26 |
| 3800 | 15 | 3800 | 22 |
| 5100 | 13 | 3500 | 19 |
| 3500 | 5 | 4300 | 14 |
| 4300 | 5 | 5100 | 10 |
| 4700 | 5 | 4900 | 8 |
| 4900 | 2 | 4200 | 6 |
| 4800 | 1 | 4700 | 5 |
| 4200 | 1 | 4800 | 5 |
| 4400 | 0 | 4400 | 0 |
| 4500 | 0 | 4500 | 0 |
| 4600 | 0 | 4600 | 0 |
| 5000 | 0 | 5000 | 0 |
| 5200 | 0 | 5200 | 0 |

TABLE IV

Correlation between redox potentials and bioactivities (as % ferredoxin), in the chloroplast/nitrogenase Assay for acetylene reduction. $E_{\frac{1}{2}}$ are Polarographic values measured in 0.1 M phosphate buffer pH 7.55, at 25.

| COMPOUND NO. | % FERREDOXIN ACTIVITY | $E_{\frac{1}{2}}$ vs. SCE (mV) |
|---|---|---|
| 1800 | 124 | −683 |
| 4100 | 110 | −720 |
| 1200 | 107 | −699 |
| 2400 | 105 | −701 |
| 700 | 104 | −700 |
| Ferredoxin | 100 | −570 |
| 3000 | 99 | −738 |
| 2600 | 98 | −730 |
| 3200 | 98 | −673 |
| 1000 | 95 | −710 |
| 1801 | 79 | −676 |
| 600 | 64 | −651 |
| 2000 | 61 | −573 |
| 2800 | 61 | −690 |
| 2200 | 55 | −704 |
| 800 | 50 | −625 |
| 300 | 41 | −683 |
| 1500 | 41 | −683 |
| 1700 | 33 | −715 |
| 3700 | 31 | −701 |
| 4000 | 28 | −685 |
| 400 | 26 | −738 |
| 500 | 22 | −751 |
| 3901 | 22 | −685 |
| 3400 | 20 | −680 |
| 200 | 17 | −699 |
| 3800 | 15 | −681 |
| 5100 | 13 | −597 |
| 3500 | 5 | −575 |
| 4300 | 5 | −696 |
| 4700 | 5 | −611 |
| 4900 | 2 | −700 |
| 4200 | 1 | −798 |
| 4800 | 1 | −655 |
| 4400 | 0 | −613 |
| 4500 | 0 | −390 |
| 4600 | 0 | −479 |
| 5000 | 0 | −676 |
| 5200 | 0 | −433 |

The following examples further illustrate the synthesis of the pyrazinium compounds of the invention. Each pyrazinium compound is identified by a number which correlates with the compound and carrier numbers given in Tables I–IV. All degrees are Celsius. NMR chemical shifts are reported as delta values. UV spectra are expressed in lambda max (nm) and log epsilon. Most column chromatographies were performed by gel permation techniques using polyacrylamide with a molecular size exclusion of 1800 Daltons, (Biogel P-2).

EXAMPLE 1

2-(1-Hydroxyethyl)pyrazine (100)

21.6 g of 2-ethylpyrazine (101) was dissolved in 300 ml of carbon tetrachloride and 35.6 g of N-bromosuccinimide added; *J. Org. Chem.*, 37, 511(1972). The mixture was heated to 75° C. and 1.5 g of dibenzoyl peroxide was added in one portion. Heating was continued for 4 hours after which the mixture was cooled and filtered into 500 ml of a 10% potassium carbonate solution.

This mixture was rapidly stirred until no 2-(1-bromoethyl)pyrazine remained (TLC silica gel/1:1 ethyl aqueous solution was acidified to pH 6, concentrated to 200 ml and continuously extracted with ethyl acetate for two days. The ethyl acetate was removed at reduced pressure and the residue distilled, giving 18.6 g of product (100). b.p. 112°–3° (13 mm). UV $H_2O$ max: 264 (3.85), 268 (3.82). $^{13}C$ NMR: 159.75, S(C2); 144.52, D, 143.99, D, 142.51, D (C3, C5, C6); 69.20, D (CHOH); 23.11, Q ($CH_3$).

EXAMPLE 2

1-Methyl-3-(1-hydroxyelhyl)pyrazinium iodide (200)

2.0 g of 2-(1-hydroxyethyl)pyrazine (100) was dissolved in 10 ml of ether and 5 ml of methyl iodide added. The flask was stoppered and stored in the dark.

After 5 days the solid was filtered, washed with ethyl acetate and dried in vacuo to give 7.8 g of product (200). Recrystallized from ethyl acetate/ethanol, m.p. 129°–30° (dec.). UV H$_2$O max: 225 (4.11), 279 (3.85). $^{13}$C NMR: 167.58, S (C3); 150.57, D (C5); 137.14, D, 136.31, D (C2, C6); 69.03, D (CHOH); 50.14, Q (NCH$_3$); 22.88, Q (CH$_3$). $^1$H NMR: 9.36, D,T(H6); 9.10, S (H2); 8.89, D (H5); 5.27, Q (CHOH); 4.52, T (NCH$_3$); 1.61, D (CCH$_3$).

EXAMPLE 3

1-Methyl-3-(2-hydroxyethyl)pyrazinium iodide (300)

2.0 g of 2-(2-hydroxyethyl)pyrazine (301) prepared by a known method by condensing formaldehyde and 2-methylpyrazine, was dissolved in 5 ml of methanol and 5 ml of methyl iodide added. The solution was refluxed for 3 days, concentrated and the residue purified by gel permeation chromatography. Freeze-drying gave 3.2 g of yellow solid product (300). It was recrystallized from ethyl acetate/ethanol, m.p. 94°–5°. UV H$_2$O max: 226 (4.13), 281 (3.85). $^{13}$C NMR: 163.25, S (C3); 150.71, D (C5); 138.69, D, 136.25, D (C2, C6); 60.38, T (CH$_2$OH); 49.88, Q (NCH$_3$); 38.75, T (—CH$_2$—). $^1$H NMR: 9.35, D, T (H6); 8.97, S (H2); 8.85, D (H5); 4.49, S (NCH$_3$); 4.08, T; 3.35, T (ArCH$_2$, CH$_2$OH).

EXAMPLE 4

1-Methyl-3-hydroxymethyl-5-methylpyrazinium iodide (400)

2.0 g of 2-hydroxymethyl-6-methylpyrazine (401), prepared by the known method of Klein, et al., *J. Org. Chem.*, 26, 126(1961), was dissolved in 5 ml of ether and 5 ml of methyl iodide added. The flask was stoppered and stored in the dark for 2 weeks. The ether was decanted and the resultant semi-solid material recrystallized from ethanol/ethyl acetate giving 1.8 g of a yellow solid, product (400) m.p. 153°–4°. UV H$_2$O max: 226 (4.13), 287 (3.89). $^{13}$C NMR: 163.33, S, 161.73, S (C3, C5); 136.85, D, 133.10, D (C2,C6); 62.79, T (CH$_2$OH); 49.74, Q (NCH$_3$); 22.19, Q (ArCH$_3$). $^1$HNMR: 8.80, S, 8.76, S (H2, H6): 4.97, S (CH$_2$OH); 4.44, S (NCH$_3$); 2.79, S (ArCH$_3$).

EXAMPLE 5

1-Methyl-3(2)-hydroxymethyl-6(5)-methylpyrazinium iodide (500)

5.0 g of 2-hydroxymethyl-5-methylpyrazine (501), a known compound prepared in a fashion similar to that for pyrazine (401) was dissolved in 10 ml of ether and 10 ml of methyl iodide added. The flask was stoppered and stored in the dark for four weeks. The solid was filtered and washed with ether giving 6.9 g of a yellow crystalline solid product (500), m.p. 135°–7°. UV H$_2$O max: 227 (4.12), 288 (3.89). $^{13}$C NMR shows that the product is a mixture of the two possible isomers.

EXAMPLE 6

1-(3-Sulfonylpropyl)-3-methylpyrazine (600)

16.0 g of 1,3-propane sultone was dissolved in 200 ml of 1:1 ether/ethyl acetate and 15.1 g of 2-methylpyrazine added. It was then stored and the solvent allowed to evaporate.

The resultant solid was taken up in 50 ml of water, washed with ethyl acetate and chromatographed (Biogel P-2 and water). Freeze-drying yields 20.5 g of product (600) which was recrystallized from ethanol/water. m.p. 218°–221° (dec.). UV H$_2$O max: 282 (3.84). $^{13}$C NMR: 163.15, S (C3); 150.69, D (C5); 137.80, D, 134.81, D (C2, C6); 61.67, T (NCH$_2$); 47.79, T (CH$_2$SO$_3^-$); 26.73, T (CH$_2$); 22.36, Q (CH$_3$). $^1$H NMR: 9.30, D, T (H6); 9.01, S (H2); 8.88, D (H5); 4.87, T (NCH$_2$); 3.03, T (CH$_2$SO$_3^-$); 2.84, S (CH$_3$); 2.50, M=5 (—CH$_2$—).

EXAMPLE 7

1-(3-Sulfonylpropyl)-2,5-dimethylpyrazine (700)

6.0 g of 2,5-dimethylpyrazine (701) and 7.0 g of 1,3-propane sultone were dissolved in 10 ml of ethyl acetate and heated at 40° C. for 2 days. The resultant solid was then filtered and washed with ethyl acetate giving 7.9 g of product (700). It was recrystallized from propanol/water, m.p. 258°–9°. UV H$_2$O max: 204 (3.94), 290 (3.85). $^{13}$C NMR: 159.25, S (C5); 152.47, D (C3); 146.91, S (C2); 136.88, D (C6); 57.84, T (NCH$_2$); 47.94, T (CH$_2$SO$_3^-$); 25.42, T (CH$_2$); 21.49, Q, 17.16, Q (ArCH$_3$). $^1$H NMR: 9.15, S (H3); 8.83, S (H6); 4.77, T (NCH$_2$); 3.09, T (CH$_2$SO$_3^-$), 2.90, S, 2.75, S (ArCH$_3$); 2.40, M=5 (—CH$_2$—).

EXAMPLE 8

1-(2-Carboxyethyl)pyrazinium bromide (800)

This product (800) was prepared by a published method, A Le Berre, et al. *Bull. Soc. Chim. France*, 2404 (1973), m.p. 189°–92° (dec), lit. m.p. 210° (dec.) UV H$_2$O max: 276 (3.79). $^{13}$C NMR: 173.65, D(C—CO$_2$H); 151.76, D(C3,C5); 138.47, D(C2,C6); 59.04, T(NCH$_2$); 34.90, T(—CH$_2$—).

EXAMPLE 9

2-(2-Sulfonylbutyl)pyrazine sodium salt (900)

2.72 g of 2-butylpyrazine and 3.56 g of N-bromosuccinimide were added to 100 ml of carbon tetrachloride and the mixture heated to 70°–5° C., then 0.3 g of dibenzoyl peroxide was added. The mixture was then refluxed for 3 hours, cooled, filtered and the filtrate concentrated in vacuo. The resultant oil was taken up in 100 ml toluene, 4.0 g of 1,8-diazabicyclo [5.4.0]undec-7-ene added and the solution refluxed overnight. It was then cooled, the toluene solution decanted and concentrated in vacuo. To the resultant olefinic compound, 2-(1-butenyl)pyrazine (901), was added a solution of 6.0 g of sodium sulfite in 100 ml of water and this mixture then refluxed 3 days. The aqueous solution was washed with chloroform, freeze-dried and taken up in 100 ml of methanol. The solution was filtered and the filtrate concentrated and purified by chromatography (Biogel P-2/water). Freeze-drying gave 3.32 g of product (900) as an amorphous solid. UV H$_2$O max: 268 (3.86), 272 (3.85).

EXAMPLE 10

1-Methyl-3-(2-sulfonylbutyl)pyrazine (1000)

3.2 g of 2-(2-sulfonylbutyl)pyrazine (900) was added to a solution of 10 ml methyl iodide/25 ml methanol and the mixture refluxed for 4 days. It was then concentrated and purified by gel permeation chromatography (Biogel P-2/water). Freeze-drying gave 2.9 g of an amorphous solid (1000) which was crystallized from ethyl acetate/propanol, m.p. 224°–5° (dec.). UV H$_2$O max: 283 (3.88).

EXAMPLE 11

2-(1-Sulfonylbutyl)pyrazine sodium salt (1100)

2.72 g of 2-butylpyrazine and 3.56 g of N-bromosuccinimide are added to 100 ml of carbon tetrachloride and the mixture heated to 70°–5° C., when 0.3 g of dibenzoyl peroxide was added. The mixture was then refluxed for 3 hours, cooled, filtered and the filtrate concentrated in vacuo. To the resultant oil, 2-(1-bromobutyl)pyrazine (1101), was added a solution of 5 g of sodium sulfite in 100 ml of water and the mixture refluxed for 2 days. It was then cooled and extracted with chloroform. The aqueous solution was freeze-dried, taken up in 100 ml of methanol and filtered. The filtrate was concentrated and purified by gel permeation chromatography (Biogel P-2/water). Freeze-drying gave 3.84 g of product (1100) which was recrystallized from propanol/water, m.p. 278°–9°. UV $H_2O$ max: 204 (3.84), 268 (3.86), 272 (3.84).

EXAMPLE 12

1-Methyl-3-(1-sulfonylbutyl)pyrazine (1200)

3.6 g of 2-(1-sulfonylbutyl)pyrazine (1100) was added to a solution of 10 ml methyl iodide/25 ml methanol and the mixture refluxed for 4 days. It was then concentrated and purified by gel permeation chromatography (Biogel P-2/water). Freeze-drying gave 3.2 g of product (1200) which was recrystallized from propanol/water, m.p. 293°–5° (dec). UV $H_2O$ max: 206 (3.87), 283 (3.90). $^1$H NMR: 9.41, D, T (H6); 9.11, S (H2); 8.94, D (H5); 4.63–4.58, M (CHSO$_3^-$); 4.52, S (NCH$_3$); 2.31, M (C$\underline{H_2}$CHSO$_3^-$); 1.27, M (C$\underline{H_2}$CH$_3$); 0.89, T (CH$_3$).

EXAMPLE 13

4-(2-Pyrazinyl)-1-butene (1300)

To a mixture of 15.6 g of sodium amide in 400 ml of ammonia was added dropwise 37.6 g of 2-methylpyrazine. The mixture was stirred for 2 hours and then 24.2 g of allyl bromide in 50 ml of ether was slowly added. This was stirred for 2 hours, 25 g of ammonium chloride added and the ammonia replaced by 500 ml of ether. 250 ml of water was added, the organic layer separated and the aqueous layer extracted twice with ether. The combined organic layers were then concentrated at reduced pressure.

The residue was fractionated by distillation to give 20.5 g of product (1300), b.p. 96°–7° (25 mm). UV 2% EtOH max: 268 (3.82), 273 (3.82).

From the above distillation was also obtained 5.4 g of a second product, characterized as the bisalkylated compound, 4-(2-pyrazinyl)-1,6-heptadiene (1301), b.p. 122°–3° (24 mm). UV 10% EtOH max: 269 (3.83), 273 (3.83).

EXAMPLE 14

2-(3,4-Dihydroxybutyl)pyrazine (1400)

4.15 g of 4-(2-pyrazinyl)-1-butene (1300) was dissolved in 100 ml of 1:1 water/acetone and cooled to 5° C. To this was slowly added a solution of 3.60 g of potassium permanganate in 300 ml of water. This was kept at 5° C. for 18 hours and then allowed to stir for 4 hours at R.T. It was adjusted to pH 7 with 5% $H_2SO_4$, filtered through celite and concentrated. Continuous extraction with chloroform for 2 days followed by evaporation of the solvent left 4.27 g of product (1400) which was distilled under vacuum, b.p. 174°–5° (0.2 mm). UV $H_2O$ max: 268 (3.76), 272 (3.76).

EXAMPLE 15

1-Methyl-3-(3,4-dihydroxybutyl)pyrazinium iodide (1500)

2.0 g of 2-(3,4-dihydroxybutyl)pyrazine (1400) was dissolved in 10 ml of methanol and 5 ml of methyl iodide added. It was refluxed for 3 days and then concentrated. It was purified by gel permeation chromatography (Biogel P-2/water) and freeze-dried to give 3.1 g of an amorphous solid product (1500). UV $H_2O$ max: 226 (4.13), 282 (3.85). $^{13}$C NMR: 165.42, S (C3); 150.57, D (C5); 138.36, D, 135.90, D (C2, C6); 71.69, D (CHOH); 66.08, T (CH$_2$OH); 49.87, Q (NCH$_3$); 32.40, T (—CH$_2$—); 31.99, T (—CH$_2$—). H NMR: 9.31, D, T (H6); 8.97, S (H2); 8.81, D (H5); 4.47, S (NCH$_3$); 3.80, M (CHOH); 3.67–3.51, M, 3.29–3.15, M, 2.05, M; 1.98–1.88, M (ArCH$_2$).

EXAMPLE 16

4-(2-Pyrazinyl)-1,2,6,7-tetrahydroxyheptane (1600)

5.40 g of 4-(2-pyrazinyl)-1,6-heptadiene (1301) was added to 100 ml of water and enough acetone added to dissolve it. It was cooled to 5° C. and a solution of 6.6 g of potassium permanganate in 300 ml of water added dropwise. It was then allowed to warm to R.T. and stirred overnight.

The pH was adjusted to 7, the solution filtered through celite and the acetone removed in vacuo. The aqueous solution was extracted with 200 ml of ether and freeze-dried.

This material was taken up in 75 ml of ethanol, filtered and the filtrate concentrated. The product was then purified by gel permeation chromatography (Biogel P-2/water) giving 6.12 g of a pale yellow oil product (1600) upon removal of the water. UV $H_2O$ max: 268 (3.70), 273 (3.69).

EXAMPLE 17

1-Methyl-3-[4-(1,2,6,7-tetrahydroxyheptyl)]pyrazinium iodide (1700)

2.0 g of 4-(2-pyrazinyl)-1,2,6,7-tetrahydroxyheptane was dissolved in 10 ml of methanol and 5 ml of methyl iodide added. This was reluxed for four days, cooled and concentrated. It was taken up in 100 ml water, washed with chloroform and freeze dried. It was purified by gel permeation chromatography (Biogel P-2/water) and freeze-dried to give 2.4 g of product (1700) as an amorphous solid. UV $H_2O$ max: 226 (4.14), 285 (3.83). $^{13}$C NMR shows that this is a mixture of three stereoisomers: 169.17, 168.18, 167.21, S (C3); 151.31, 150.95, 150.62, D (C5); 138.2, M, 136.64, 136.25, 135.86, D (C2, C6); 71.07, 70.83, D (CHOH); 69.79, 69.62, D (CHOH); 66.45, 66.36, 66.28, T (CH$_2$OH); 49.86, Q (NCH$_3$); 41.53, 39.93, 38.83, D (—CH—); 38.91, 38.55, 38.43, 37.72, T (—CH$_2$—).

EXAMPLE 18

4-(1-Methyl-3-pyrazinyl)heptane-1,7-disulfonate sodium salt (1800) and
1-Methyl-3-(4-sulfonylbutyl)pyrazine (1801)

To a suspension of sodium amide (from 2.3 g of sodium) in 150 ml of ammonia was added dropwise 9.4 g of methylpyrazine. The resultant blood red solution was stirred for 2 hours and then a solution of 6.1 g of propane sultone in 20 ml of ether slowly added. This was stirred for 2 hours, 5 g of ammonium chloride added, and the ammonia replaced with ether. 500 ml of water was then added, the pH adjusted to 7, and the aqueous solution extracted twice with ether and freeze-dried, giving a crude mixture of two products [which could be separated by chromatography (Biogel P-2/water)]. It was desalted by passage down a Biogel P-2 column, freeze-dried, and then taken up in a minimum of methanol with a little water added to aid in its dissolution. To this was added 50 ml of methyl iodide and the solution refluxed until the starting material was gone (loss of UV $H_2O$ max 267). The solvent was removed and the product mixture was separated by chromatography (C18R.P./water) followed by freeze-drying to give two products (1800) and (1801):

(a) 3.8 g of 4-(1-methyl-3-pyrazinyl)heptane-1,7-disulfonate sodium salt (1800) as an amorphous solid. UV $H_2O$ max: 282 (3.83). $^{13}C$ NMR; 165.43, S (C3); 150.56, D (C5); 138.42, D, 135.96, D (C2, C6); 60.05, D (—CH—); 51.64, 35.74, 29.24, 29.06, 26.13, 22.16, T (—CH$_2$—); 49.72, Q (NCH$_3$).

(b) 4.2 g of 1-methyl-3-(4-sulfonylbutyl)pyrazine (1801) as an amorphous solid. UV $H_2O$ max: 282 (3.84). $^{13}C$ NMR: 165.39, S (C3); 150.55, D (C5); 138.29, D, 135.96, D (C2, C6); 51.31, T (CH$_2$SO$_3^-$); 49.49, Q (NCH$_3$); 35.41, T (ArCH$_2$); 27.59, T, 24.24, T (—CH$_2$—). $^1H$ NMR: 9.29, D, T (H6); 8.94, S (H2); 8.79, D (H5); 4.46, S (NCH$_3$); 3.16, T (CH$_2$SO$_3^-$); 2.99–2.94, M (ArCH$_2$); 1.96, M ($\underline{CH_2}$CH$_2$SO$_3^-$); 1.81, M (ArCH$_2\underline{CH_2}$).

EXAMPLE 19

Pyrazine-2-sulfonic acid sodium salt (1900)

4.5 g of chloropyrazine was added to a solution of 8 g of sodium sulfite in 100 ml of water. This mixture was refluxed for 3 days, cooled and washed with chloroform. The aqueous solution was then freeze-dried and taken up with 200 ml of methanol and filtered. The filtrate was concentrated and purified by gel permeation chromatography (Biogel P-2/water). Freeze-drying gave 6.2 g of product (1900), m.p. 299°–302° (dec). UV $H_2O$ max: 203 (3.79), 267 (3.79).

EXAMPLE 20

1-Methyl-3-sulfonylpyrazine (2000)

4.0 g of Pyrazine-2-sulfonic acid sodium salt (1900) was added to a solution of 20 ml methyl iodide/40 ml methanol and the mixture refluxed for 7 days. The solvent was evaporated and the residue chromatographed (Biogel P-2/water) giving 3.5 g of product (2000) which was recrystallized from ethanol/water, m.p. 270°–2° (dec). UV $H_2O$ max: 282 (3.86).

EXAMPLE 21

2-(1,2-Dihydroxyethyl)pyrazine (2100)

10.6 g of 2-vinylpyrazine prepared by the procedure of M. R. Kamal, et al., *J. Org. Chem.*, 27, 1363 (1962), was dissolved in 100 ml of water and cooled to 2°–4° C. under an atmosphere of N$_2$. To this a solution of 15.8 g of potassium permanganate in 500 ml of water was slowly added (4 hours) with efficient stirring and continued cooling. Following completion of the addition, the mixture was cooled to 5° and stored overnight. The cooled mixture was adjusted to pH 7 with 5% sulfuric acid and the precipitate filtered and washed with 100 ml of water. Freeze-drying of the aqueous solution left 20.3 g of a spongy solid. This material was stirred for 4 hours with 500 ml of absolute ethanol and the salts removed by filtration and washed with 50 ml of ethanol. Evaporation of the ethanol yielded 13.6 g of material which was 93% pure by HPLC analysis, the remainder being pyrazine-2-carboxylic acid. Purification of the product was accomplished by chromatography using the Waters Prep LC 500 with two C18 reverse phase columns and 3% methanol/water as the eluent. Removal of the solvent left 10.6 g of product (2100) as a light yellow, viscous oil. UV $H_2O$ max: 265 (3.86), 270 (3.82), 298 (2.87).

EXAMPLE 22

1-Methyl-3-(1,2-dihydroxyethyl)pyrazinium iodide (2200)

2.8 g of 2-(1,2-dihydroxyethyl) pyrazine (2100) was dissolved in 20 ml of methanol, 10 ml of methyl iodide added and the solution refluxed for 3 days. The solvent was then removed, the residue taken up in 100 ml of water and washed with chloroform. The aqueous solution was concentrated and purified by gel permeation chromatography (Biogel P-2/water). Freeze-drying yielded 3.7 g product (2200) which was recrystallized from ethyl acetate/ethanol, m.p. 105°–6°. UV $H_2O$ Max: 227 (4.13), 281 (3.83).

EXAMPLE 23

2-(1-Sulfonylethyl)pyrazine sodium salt (2300)

5.4 g of 2-ethylpyrazine was dissolved in 100 ml of carbon tetrachloride and 8.9 g of N-bromosuccinimide added. This mixture was heated to 70°–5° C., 0.5 g dibenzoyl peroxide added and the mixture refluxed for 3 hours. It was then cooled, filtered and the filtrate concentrated in vacuo. To the resultant oil was added 10 g of sodium sulfite/100ml of water and the mixture refluxed for 3 days. It was then cooled, washed with chloroform and freeze-dried. The resultant solid was taken up in 200 ml of methanol, filtered and the filtrate concentrated. It was purified by gel permeation chromatography (Biogel P-2/water) and freeze-dried to give 9.2 g product (2300). It was recrystallized from methanol, m.p. 258°–62°. UV $H_2O$ max: 203 (3.90), 267 (3.87), 272 (3.85). $^{13}C$ NMR: 153.54, S (C2); 145.76, D, 144.97, D, 144.14, D (C3, C5, C6); 61.14, D (—CH—); 15.18, Q (CH$_3$).

EXAMPLE 24

1-Methyl-3-(1-sulfonylethyl)pyrazine (2400)

3.50 g of 2-(1-sulfonylethyl)pyrazine sodium salt (2300) was dissolved in 75 ml of methanol and 10 ml of methyl iodide added. The flask was then stoppered and stored in the dark at room temperature.

After one week the solvent was removed under reduced pressure, the residue taken up in water and washed twice with ethyl acetate. The aqueous solution was concentrated and chromatographed (Biogel P-2/water). Freeze drying gave 3.37 g of product (2400). It was recrystallized from ethanol/water, m.p. 270°–2° (dec.). UV $H_2O$ max: 282 (3.85), 203 (3.84). $^{13}C$ NMR: 160.27, S (C3); 150.66, D (C5); 139.29, D, 137.22, D (C2, C6); 61.25, D (—CH—); 49.94, Q (N—CH$_3$); 14.58, Q (—CH$_3$). $^1H$ NMR: 9.37, D, T (H6); 9.11, S (H2); 8.91, D (H5); 4.72, Q (—CH—); 4.51, T (NCH$_3$); 1.80, D (CH$_3$).

EXAMPLE 25

2-(2-Sulfonylethyl)pyrazine sodium salt (2500)

Vinylpyrazine was prepared by a known procedure M. R. Kamal, et al. *J. Org. Chem.*, 27, 1363 (1962). 7.0 g of vinylpyrazine was dissolved in 300 ml of ether and a solution of 8.3 g of sodium sulfite in 100 ml of water added with rapid stirring. After several days at R.T. the reaction mixture was heated to 50° C. and an additional 10.0 g of sodium sulfite added. Upon completion (TLC silica gel/ethyl acetate), the reaction was cooled, washed with ether and concentrated. It was then taken up in 600 ml of methanol, filtered and the filtrate concentrated. The product was purified by chromatography (Biogel P-2/water) giving 13.0 g of white powder product (2500) following freeze-drying. It was recrystallized from methanol, m.p. 350°. UV $H_2O$ max: 267 (3.81), 272 (3.81), 300 (2.90). $^{13}C$ NMR: 155.73, S (C2); 145.21, D, 144.86, D, 143.13, D (C3, C5, C6); 50.55, T ($CH_2SO_3^-$); 30.68, T ($ArCH_2$).

EXAMPLE 26

1-Methyl-3-(2-sulfonylethyl)pyrazine (2600)

5.0 g of 2-(2-sulfonylethyl)pyrazine sodium salt (2500) was added to a solution of 10 ml methyl iodide/50 ml methanol and the mixture refluxed for 4 days. It was then concentrated and purified by gel permeation chromatography (Biogel P-2/water). Freeze-drying gave 4.5 g of product (2600). It was recrystallized from ethanol/water, m.p. 255–60 (dec.). UV $H_2O$ max: 281 (3.87). $^{13}C$ NMR: 162.99, S (C3); 150.63, D (C5); 138.51, D, 136.24, D (C2, C6); 49.66, Q ($NCH_3$); 49.56, T ($CH_2SO_3$); 31.44, T ($ArCH_2$). $^1H$ NMR: 9.33, D,T (H6); 8.99, S (H2); 8.82, D (H5); 4.48, S ($NCH_3$); 3.58–3.43, M (—$CH_2$—).

EXAMPLE 27

2-Sulfonylmethylpyrazine sodium salt (2700)

A mixture of 4.7 g of 2-methylpyrazine, 200 ml of carbon tetrachloride and 8.9 g of N-bromosuccinimide was heated to 70°-5° C. and 6.1 g of dibenzoyl peroxide added. It was then refluxed for 5 hours, cooled and filtered. The filtrate was concentrated, a solution of 10 g sodium sulfite/100 ml water added and the mixture refluxed for 3 days. It was then continuously extracted overnight with chloroform, freeze-dried and the resultant solid taken up in 250 ml of methanol. This was filtered, the filtrate concentrated and chromatographed (Biogel P-2/water) to give 3.9 g of product (2700). It was recrystallized from ethanol/water, m.p. 294°-9°. UV $H_2O$ max: 203 (3.84), 267 (3.84), 272 (3.83). $^{13}C$ NMR: 149.23, S (C2), 146.44, D, 145.23, D, 144.22, D (C3, C5, C6); 57.03, T ($CH_2SO_3^-$).

EXAMPLE 28

1-Methyl-3-sulfonylmethylpyrazine (2800) 3.0 g of 2-sulfonylmethylpyrazine (2700) was added to a solution of 10 ml methyl iodide/25 ml methanol and refluxed for 3 days. The mixture was cooled, and the filtrate concentrated. The solid was then chromatographed (Biogel P-2 and water) and freeze-dried giving 2.5 g of product (2800). It was recrystallized from propanol/water, m.p. >240° (dec.) UV $H_2O$ max: 282 (3.89). $^{13}C$ NMR: 156.04, S (C3); 150.99, D (C5); 139.63, D, 137.42, D (C2, C6); 57.10, T ($CH_2SO_3$); 50.01, Q ($NCH_3$). $^1H$ NMR: 9.40, D, T (H6); 9.12, S (H2); 8.96, D (H5); 4.67, S ($CH_2SO_3^-$); 4.54, S ($NCH_3$).

EXAMPLE 29

2-Sulfonylmethyl-6-methylpyrazine sodium salt (2900)

A mixture of 5.4 g of 2,6-dimethylpyrazine and 8.9 g of N-bromosuccinimide in 200 ml of carbon tetrachloride was heated to 75° and 6.1 g of dibenzoyl peroxide added. It was refluxed 6 hours, cooled, filtered and the filtrate concentrated. To this concentrate was added 10 g sodium sulfite/100 ml water and the mixture refluxed for 4 days. This aqueous solution was then continuously extracted overnight with chloroform, freeze-dried and the resultant solid taken up in 250 ml of methanol. It was filtered, the filtrate concentrated and chromatographed (Biogel P-2/water) to give 4.8 g of product (2900). It was recrystallized from ethanol/water, m.p. 282°-5° (dec.). UV $H_2O$ max: 208 (3.80), 276 (3.88).

EXAMPLE 30

1-Methyl-3-sulfonylmethyl-5-methylpyrazine (3000)

4.0 g of 2-sulfonylmethyl-6-methylpyrazine sodium salt (2900) was added to a solution of 15 ml methyl iodide/30 ml methanol and the mixture refluxed for 4 days. It was then cooled and filtered. The solid was chromatographed (Biogel P-2/water) and freeze-dried to give 3.4 g of product (3000). It was recrystallized from propanol/water, m.p. >280° (dec.). UV $H_2O$ max: 288 (3.92).

EXAMPLE 31

2-Sulfonylmethyl-5-methylpyrazine sodium salt (3100)

A mixture of 3.3 g of 2,5-dimethylpyrazine and 5.4 g of N-bromosuccinimide in 150 ml of carbon tetrachloride was heated to 75° and 3.7 g of dibenzoyl peroxide added. This solution was refluxed for 6 hours, cooled and filtered. The filtrate was concentrated and a solution of 10 g sodium sulfite/100 ml water added. This mixture was refluxed for 3 days and then continuously extracted overnight with chloroform. The aqueous layer was freeze-dried, taken up in 150 ml of methanol and filtered. The filtrate was concentrated and chromatographed (Biogel P-2/water) giving 3.1 g of an amorphous solid. It was crystallized from propanol/water, to yield product (3100) m.p. >200° (dec.). UV $H_2O$ max: 209 (3.89), 278 (3.85).

EXAMPLE 32

1-Methyl-3-sulfonylmethyl-6-methylpyrazine (3200)

2.0 g of 2-sulfonylmethyl-5-methylpyrazine sodium salt (3100) was added to a solution of 15 ml methyl iodide/25 ml methanol and refluxed for 5 days. The mixture was then cooled and filtered. The solid was purified by gel permeation chromatography (Biogel P-2/water) and freeze-dried to give 1.6 g of product (3200). It was recrystallized from propanol/water, m.p. >350° (dec.) UV H$_2$O max: 213 (3.91), 293 (3.87).

EXAMPLE 33

2-(2-Hydroxybutyl)pyrazine (3300)

To a suspension of sodium amide (from 11.5 g of sodium) in 1 liter of ammonia was added 47 g of 2-methylpyrazine. This was stirred for 1 hour and then a solution of 15 g of propionaldehyde in 25 ml of ether added dropwise. This was then stirred for 2 hours, 50 g of ammonium chloride slowly added and the ammonia replaced with ether. 250 ml of water was added and the product extracted with ethyl acetate, dried over sodium sulfate and concentrated. The residue was then distilled to yield 12.7 g of product (3300). b.p. 141°-3° (16 mm). UV H$_2$O max: 267 (3.80), 272 (3.79). $^{13}$C NMR: 155.90, S (C2); 145.89, D, 144.68, D, 142.88, D (C3, C5, C6); 73.37, D (CHOH); 42.28, T (ArCH$_2$); 29.98, T (—CH$_2$—): 9.97, Q (CH$_3$).

EXAMPLE 34

1-Methyl-3-(2-hydroxybutyl)pyrazinium iodide (3400)

3.1 g of 2-(2-hydroxybutyl)pyrazine (3300) was dissolved in 30 ml of methanol, 10 ml of methyl iodide added and the solution refluxed for 3 days. It was then concentrated, taken up in water and extracted with chloroform. The aqueous solution was concentrated and chromatographed (Biogel P-2/water). Freeze-drying gave 4.6 g of product (3400) as a yellow solid. It was recrystallized from ethyl acetate/ethanol, m.p. 108°-9°. UV H$_2$O max: 227 (4.11), 282 (3.85). $^{13}$C NMR: 163.30, S (C3); 150.63, D (C5); 138.77, D, 136.12, D (C2, C6); 72.66, D (CHOH); 49.93, Q (NCH$_3$); 43.02, T, 30.11, T (—CH$_2$—); 9.97, Q (CH$_3$). $^1$H NMR: 9.35, D, T (H6); 8.95, S (H2); 8.85, D (H5); 4.49, S (NCH$_3$); 4.11, M (CHOH); 3.39-3.14, M (ArCH$_2$); 1.75-1.52, M (—CH$_2$—); 0.99, T (CH$_3$).

EXAMPLE 35

1-Methyl-3-(2-oxybutyl)pyrazinium iodide (3500)

4.0 g of 2-(2-oxybutyl)pyrazine, prepared by Jones oxidation of 2-(2-hydroxybutyl)pyrazine (3300) or by the method of J. D. Behun, et al., *J. Am. Chem. Soc.*, 81, 5157 (1959), was dissolved in 10 ml of ethyl acetate and 10 ml of methyl iodide added. This solution was stoppered and stored in the dark. The resultant semi-solid material was taken up in water, washed with ethyl acetate and freeze-dried to give 4.6 g of a hygroscopic powder product (3500) m.p. 67°-9°. UV H$_2$O max: 226 (4.18), 280 (3.84).

EXAMPLE 36

2-(1-Nitroisopropyl)pyrazine (3600)

10.8 g of 2-ethylpyrazine was dissolved in 200 ml of carbon tetrachloride, 17.8 g of N-bromosuccinimide added and the mixture heated to 75° C. To this mixture was added 1 g of dibenzoyl peroxide and the mixture refluxed for 4 hours. It was then cooled, filtered and the solvent removed at reduced pressure. To the concentrate was added a solution of 0.1 mole sodium nitromethylate in 250 ml methanol and the mixture refluxed for 2 days. The resultant mixture was cooled, filtered and the filtrate concentrated. The residue was chromatographed (C$_{18}$/water) and freeze-dried to give 4.9 g of a pale yellow oil product (3600). UV H$_2$O max: 266 (3.89), 270 (3.86).

EXAMPLE 37

1-Methyl-3-(1-nitroisopropyl)pyrazinium iodide (3700)

2.0 g of 2-(1-nitroisopropyl)pyrazine (3600) was dissolved in 10 ml of methanol, 5 ml of methyl iodide added and the solution refluxed for 4 days. The solvent was removed and the residue was taken up in water and washed with chloroform. It was then chromatographed (Biogel P-2/water) and freeze-dried giving 3.2 g of product (3700). It was recrystallized from ethyl acetate/ethanol, m.p. 135°-6°. UV H$_2$O max: 227 (4.18), 281 (3.89).

EXAMPLE 38

1-Methyl-3-(2-acetamidoethyl)pyrazinium iodide (3800)

3.0 g of 2-(2-acetamidoethyl)pyrazine, prepared by the method of G. M. Singerman, et. al., *J. Org. Chem.*, 30, 4379 (1965), was dissolved in 10 ml of ether and 10 ml of methyl iodide added. The flask was stoppered and stored in the dark for 2 weeks. The resultant solid was filtered, washed with ether and dried in vacuo to give 3.4 g of a yellow solid product (3800). It was recrystallized from ethyl acetate/ethanol, m.p. 138°-9°. UV H$_2$O max: 226 (4.17), 281 (3.85).

EXAMPLE 39

1-Methyl-3-(2-carboxyethyl)pyrazinium iodide (3900)

2.0 g of 2-(2-carboxyethyl)pyrazine prepared by the method of Jones, et. al., *J. Am. Chem. Soc.*, 72, 3539 (1950) was dissolved in 15 ml of methanol and 1.2 ml of methyl iodide added. The solution was refluxed for 3 days, cooled and concentrated. The resultant amorphous solid was crystallized from propanol, giving 3.5 g of 1-methyl-3-(2-carbomethoxyethyl)pyrazinium iodide, (3901) m.p. 108°-9°, UV H$_2$O max: 226 (4.14), 281 (3.86).

1.0 g of 1-methyl-3-(2-carbomethoxyethyl)-pyrazinium iodide was dissolved in 30 ml of 2N HCl and refluxed overnight. It was then concentrated, taken up in 100 ml of water and washed with methylene chloride. Concentration of the aqueous solution gave 0.55 g of 1-methyl-3-(2-carboxyethyl)pyrazinium iodide (3900) as an amorphous solid. UV H$_2$O max: 226 (4.12), 281 (3.85).

EXAMPLE 40

1-Methyl-3-(2-carboxamidoethyl)pyrazinium iodide (4000)

0.75 g of 2-(2-carboxamidoethyl)pyrazine prepared by the method of Jones as given in Example 39 was dissolved in 8 ml of methanol and 1.0 g of methyl iodide added. This was refluxed overnight during which time a yellow precipitate appeared. The mixture was cooled and the solid filtered and washed with ethyl acetate. This gave 0.90 g of 1-methyl-3-(2-carboxamidoethyl)pyrazinium iodide (4000). It was recrystallized from ethyl acetate/ethanol, m.p. 172°-3°. UV H$_2$O max: 226 (4.13), 281 (3.86).

EXAMPLE 41

1-Methyl-3-(2-sulfonoxy-3,4-dihydroxybutyl)pyrazine (4100)

(a) 9.2 g of 2-(3,4-dihydroxybutyl)pyrazine (1400) was dissolved in 450 ml of 1:1 pyridine/acetic anhydride and stirred for 2 days at 25°. The solution was concentrated in vacuo, 250 ml of ice water added and then extracted with 2×250 ml of ethyl acetate. The combined organic layers were dried over Na₂SO₄ (anh.), concentrated, and the residue distilled to give 11.5 g of 2-(3,4 diacetoxybutyl)pyrazine, (4101) b.p. 141°-2° (0.4 mm).

(b) 6.0 g of 2-(3,4-diacetoxybutyl)pyrazine (4101) was dissolved in 100 ml of carbon tetrachloride and 4.24 g of N-bromosuccinimide added. This mixture was warmed to 75°, 2.90 g of dibenzoyl peroxide added and the reaction mixture refluxed for three hours. Following cooling the mixture was filtered, the filtrate concentrated in vacuo and the residue chromatographed on silica gel (hexane, then hexane/ethyl acetate). This gave 7.0 g of a mixture of two diasteriomeric bromides (4102 and 4103). These were not separated but were used directly in the next step.

(c) 7.0 g of 2-(1-bromo-3,4-diacetoxybutyl)pyrazine (4102 and 4103) was dissolved in 100 ml of toluene, 3.3 g of 1,8-diazabicyclo [5.4.0]undec-7-ene added under an argon atmosphere and the solution heated overnight at 65°-70°. It was then cooled, the toluene solution decanted and concentrated in vacuo. The residue was chromatographed on silica gel (hexane/ethyl acetate) to yield 3.5 g of 2-(3,4-diacetoxy-1-butenyl)pyrazine (4104) as a pale yellow oil. UV EtOH max: 240 (4.14), 292 (3.85), 298 (3.86).

(d) 2.60 g of 2-(3,4-diacetoxy-1-butenyl)pyrazine (4104) was added to a solution of 78 mg of sodium in 50 ml of methanol. This was stirred at 25° overnight and then concentrated in vacuo. The product was purified by gel permeation chromatography (Biogel P-2/water) and gave 1.71 g of 2-(3,4-dihydroxy-1-butenyl)pyrazine (4105) as a pale yellow oil. UV H₂O max: 234 (4.08), 292 (3.86).

(e) 1.7 g of 2-(3,4-dihydroxy-1-butenyl)pyrazine (4105) was added to 25 ml of a 10% sodium sulfite solution and refluxed until the starting olefinic material was gone. The solution was then cooled, concentrated and purified by gel permeation chromatography (Biogel P-2/water) giving 2.4 g of 2-(2-sulfonyl-3,4-dihydroxybutyl)pyrazine sodium salt as a mixture of diastereoisomers (4106 and 4107). UV H₂O max: 267 (3.86), 272 (3.85).

(f) 1.2 g of 2-(2-sulfonyl-3,4-dihydroxybutyl) pyrazine sodium salt (4106 and 4107) was added to a solution of 10 ml of methyl iodide in 25 ml of methanol. 2 ml of water were added and the mixture was refluxed for 5 days. It was then concentrated, taken up in 100 ml of water and washed with methylene chloride. The aqueous layer was concentrated and the residue chromatographed (Biogel P-2/water) giving 1.1 g of 1-methyl-3-(2-sulfonyl-3,4-dihydroxybutyl)pyrazine (4100) as a mixture of diastereoisomers. UV H₂O max: 283 (3.88). These were separated using a Biorad AG-50 W×4 (Ca++) column at 65° with water as the eluent. ¹³C NMR: 163.89, S (C3); 150.36, D (C5); 138.88, D, 135.81, D (C2, C6); 71.05, D (CHOH); 64.41, T (CH₂OH); 61.64, D (CHSO₃−); 49.65, Q (NCH₃); 32.61, T (—CH₂—). ¹³C NMR of the epimer; 163.49, S (C3); 150.44, D (C5); 138.77, D, 135.92, D (C2, C6); 71.82, D (CHOH); 63.37, T (CH₂OH); 63.25, D (CHSO₃−); 49.65, Q (NCH₃); 33.26, T (—CH₂—).

EXAMPLES 42-52

1-Methyl Pyrazinium Compounds

Additional pyrazinium compounds were prepared following known literature procedures similar to those described in the foregoing examples. The compounds are summarized as follows:

| Example | Name |
|---|---|
| 42 | 1,2,5,6 tetramethyl-3-hydroxy methylpyrazinium iodide 4200 |
| 43 | 1,3-dimethylpyrazinium iodide 4300 |
| 44 | 1-methyl-3-carboxy pyrazinium iodide 4400 |
| 45 | 1-methyl-3-methoxycarbonyl pyrazinium iodide 4500 |
| 46 | 1-methyl-3-carbamido pyrazinium iodide 4600 |
| 47 | 1-methyl-3-(methylsulfonylmethyl) pyrazinium iodide 4700 |
| 48 | 1-methyl-3-(methoxythiaacetyl) pyrazinium iodide 4800 |
| 49 | 1-methyl-3-ethylpyrazinium iodide 4900 |
| 50 | 1-methyl-3-butylpyrazinium iodide 5000 |
| 51 | 1-methyl-3-vinylpyrazinium iodide 5100 |
| 52 | [(1-methyl)benzopyrazinium] methyl sulfonate 5200 |

What is claimed is:

1. A monoquaternized pyrazinium compound of the formula:

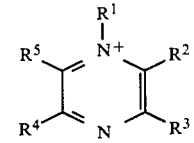

wherein:
R¹ is alkyl of 1 to 3 carbons, or (carboxy)alkyl of 2 to 4 carbons;
R², R⁴ and R⁵ are independently selected from hydrogen, and alkyl of 1 to 3 carbons;
R³ is sulfonoxy or a group of the formula (CH₂)ₙCHXY wherein
X is hydrogen, hydroxy, carboxy, carboxamido, sulfonoxy, (sulfonoxy)alkyl of 1 to 3 carbons, (carboxy) alkyl of 2 to 4 carbons or dihydroxyalkyl of 2 to 3 carbons;
Y is hydrogen, (sulfonoxy)alkyl of 1 or 3 carbons, dihydroxyalkyl of 2 to 3 carbons or alkyl of 1 to 3 carbons; and n is a whole number from 0 to 3; or n is a whole number from 0 to 6 when either of X or Y constitutes a sulfonoxy group or a (sulfonoxy)alkyl group or when X and Y together constitute multiple polar groups;
provided that
when R¹ is alkyl, R³ is other than alkyl; and
when R¹ and R³ together contain other than a carboxy or sulfonoxy substituent, an anion is also present.

2. A compound according to claim 1 wherein R¹ is alkyl.

3. A purified, isolated form of a compound according to claim 1.

4. A compound according to claim 1 wherein $R^3$ is a group of the formula —$(CH_2)_n$CHXY.

5. A compound according to claim 1 wherein $R^3$ is sulfonoxy or —$(CH_2)_n$CHXY and X is hydroxy, carboxy, carboxamido, sulfonoxy, (sulfonoxy)alkyl, (carboxy)alkyl or dihydroxyalkyl.

6. A compound according to claim 5 wherein $R^3$ is —$(CH_2)_n$CHXY.

7. A compound according to claim 5 wherein $R^1$ is alkyl.

8. A compound according to claim 6 wherein X is hydroxy, sulfonoxy, (sulfonoxy)alkyl or dihydroxyalkyl.

9. A compound according to claim 6 wherein $R^1$ is alkyl.

10. A compound according to claim 8 wherein $R^1$ is alkyl.

11. A compound according to claim 7 wherein $R^2$ is hydrogen.

12. A compound according to claim 1 wherein $R^2$ is hydrogen.

13. A compound according to claim 1 wherein $R^3$ is sulfonoxy or —$(CH_2)_n$CHXY; and X is hydroxy, sulfonoxy or (sulfonoxy)alkyl.

14. A compound according to claim 13 wherein $R^3$ is —$(CH_2)_n$CHXY.

15. A compound according to claim 14 wherein Y is hydrogen, (sulfonoxy)alkyl or dihydroxyalkyl.

16. A compound according to claim 13 wherein $R^2$ is hydrogen.

17. 1-Methyl-3-(1-hydroxyethyl)pyrazinium iodide according to claim 1.

18. 1-Methyl-3-(2-hydroxyethyl) pyrazinium iodide according to claim 1.

19. 1,5-Dimethyl-3-hydroxymethyl pyrazinium iodide according to claim 1.

20. 1,6(5) Dimethyl-3(2)-hydroxymethylpyrazinium iodide according to claim 1.

21. 1-Methyl-3-(2-sulfonoxybutyl)pyrazine according to claim 1.

22. 1-Methyl-3-(1-sulfonoxybutyl)pyrazine according to claim 1.

23. 1-Methyl-3-(3,4-dihydroxybutyl)pyrazinium iodide according to claim 1.

24. 1-Methyl-3-(1,2,6,7-tetrahydroxyhept-4-yl) pyrazinium iodide according to claim 1.

25. Sodium 4-(1-Methyl-3-pyrazinyl)heptane-1,7-disulfonate according to claim 1.

26. 1-Methyl-3-(4-sulfonoxybutyl)pyrazine according to claim 1.

27. 1-Methyl-3-sulfonoxypyrazine according to claim 1.

28. 1-Methyl-3-(1,2-dihydroxyethyl)pyrazinium iodide according to claim 1.

29. 1-Methyl-3-(1-sulfonoxyethyl)pyrazine according to claim 1.

30. 1-Methyl-3-(2-sulfonoxymethyl)pyrazine according to claim 1.

31. 1-Methyl-3-sulfonoxymethylpyrazine according to claim 1.

32. 1,5-Dimethyl-3-sulfonoxymethylpyrazine according to claim 1.

33. 1,6-Dimethyl-3-sulfonoxymethylpyrazine according to claim 1.

34. 1-Methyl-3-(2-hydroxybutyl)pyrazinium iodide according to claim 1.

* * * * *